(12) United States Patent
Borer et al.

(10) Patent No.: US 9,193,968 B2
(45) Date of Patent: Nov. 24, 2015

(54) LIBRARY COMPOSITIONS AND METHODS FOR ACYCLIC IDENTIFICATION OF APTAMERS

(75) Inventors: Philip N. Borer, Syracuse, NY (US); Mark P. McPike, Syracuse, NY (US)

(73) Assignee: APTAMATRIX, INC., Syracuse, NY (US)

(*) Notice: Subject to any disclaimer, the term of this patent is extended or adjusted under 35 U.S.C. 154(b) by 57 days.

(21) Appl. No.: 13/582,351

(22) PCT Filed: Mar. 1, 2011

(86) PCT No.: PCT/US2011/026764
§ 371 (c)(1),
(2), (4) Date: Jan. 11, 2013

(87) PCT Pub. No.: WO2011/109451
PCT Pub. Date: Sep. 9, 2011

(65) Prior Publication Data
US 2013/0217582 A1  Aug. 22, 2013
US 2015/0259673 A9  Sep. 17, 2015

Related U.S. Application Data

(63) Continuation-in-part of application No. 12/922,173, filed as application No. PCT/US2009/037022 on Mar. 12, 2009.

(60) Provisional application No. 61/035,844, filed on Mar. 12, 2008, provisional application No. 61/119,777, filed on Dec. 4, 2008, provisional application No. 61/339,193, filed on Mar. 1, 2010.

(51) Int. Cl.
C12Q 1/68 (2006.01)
C40B 40/06 (2006.01)
C12N 15/10 (2006.01)
C12N 15/115 (2010.01)
C40B 30/04 (2006.01)

(52) U.S. Cl.
CPC ........ *C12N 15/1034* (2013.01); *C12N 15/1048* (2013.01); *C12N 15/115* (2013.01); *C12Q 2525/205* (2013.01); *C12Q 2541/101* (2013.01); *C40B 30/04* (2013.01); *C40B 40/06* (2013.01)

(58) Field of Classification Search
CPC ............... C12Q 2541/101; C12Q 2525/205; C12N 15/1048; C12N 15/115; C12N 15/1034; C40B 40/06; C40B 30/04
See application file for complete search history.

(56) References Cited

FOREIGN PATENT DOCUMENTS

WO   WO2009151688   * 12/2009

OTHER PUBLICATIONS

Nutiu et al.(2005). Angewandte Chemie, 117(7), 1085-1089.*

* cited by examiner

*Primary Examiner* — Jeremy C Flinders
(74) *Attorney, Agent, or Firm* — Duan Wu; Milstein, Zhang & Wu LLC

(57) ABSTRACT

The present invention provides improved aptamer libraries useful for discovery of aptamers that have high binding affinity for a single or a plurality of targets. The libraries contain higher copies of each member candidate such that they are more likely to be available to the application of acyclic identification methods that obviate the most time-consuming and costly step in traditional SELEX method, the multiple cycles of evolutionary selection.

7 Claims, 3 Drawing Sheets

LIBRARY COMPOSITIONS AND METHODS FOR ACYCLIC IDENTIFICATION OF APTAMERS

CROSS-REFERENCE TO RELATED APPLICATIONS

This application is a continuation-in-part of U.S. nonprovisional patent application Ser. No. 12/922,173 which is a 371 national stage application of PCT/US09/37022 with an international filing date of Mar. 12, 2009 which in turn, claims priority to and the benefit of both U.S. provisional patent applications 61/035,844 filed on Mar. 12, 2008 and 61/119,777 filed on Dec. 4, 2008; this application also is a 371 national stage application of PCT/US11/26764 with an international filing date of Mar. 1, 2011 which claims priority to and the benefit of U.S. provisional patent application Ser. No. 61/339,193 filed on Mar. 1, 2010, the entire contents of which application is incorporated herein by reference.

GOVERNMENT GRANT

This invention described herein was sponsored by the U.S. government grant NIH R43 A1075739-01, the U.S. government has certain rights to this application.

FIELD OF THE INVENTION

The invention relates to the field of aptamers and their use.

BACKGROUND OF THE INVENTION

Aptamers are nucleic acids or peptide molecules that bind targets with an affinity and specificity that rival antibody-antigen interactions. DNA/RNA aptamers promise to provide a cost-effective alternative to antibodies because there is no need for selection in animals or cell lines, they have shelf-lives of years, and they can be easily modified to reduce cross-reactivity with undesired targets. This ability to bind, and in some instances, alter their targets' functions have earned aptamers potential applications in biosensor development, affinity chromatography and recently therapeutics and diagnostics.

Traditionally, artificial aptamer sequences are discovered by SELEX (Systematic Evolution of Ligands by EXponential Enrichment) and other closely related methods of in vitro evolution. Starting libraries have relatively long oligomers of DNA/RNA sequences (80-120 nt) with central randomized regions (30-120 nt). These are sparsely represented libraries with a probability of $\sim 10^{-4}$ that any particular sequence occurs in a typical starting pool for a randomized 30 mer, and of $\sim 10^{-29}$ with randomized 70 mers. This means that nearly all SELEX experiments begin with single copies of those sequences that are present by random chance. Evolution occurs via the selective pressure of binding to a target followed by amplification of the survivors; selection and amplification are repeated in typically 5-20 rounds. Winning aptamers are found by cloning and sequencing, after which a minimal core binding sequence is sought by truncating segments of the parent aptamer that are not needed for the interaction with the target.

Despite the wide adoption of the SELEX procedure for their discovery, DNA/RNA aptamers for only a few hundred targets have been discovered to date using this method compared with the discovery of thousands of antibodies during the same period. This limited success may stem primarily from a significant number of drawbacks with the SELEX method itself. Particularly relevant here, the SELEX methodology of repeated rounds of selection and amplification are cumbersome, time-consuming and very expensive. There is a need for faster and less expensive methods of aptamer discovery and improvement.

SUMMARY OF THE INVENTION

A major goal of this invention is to provide improved libraries for both newer and more traditional ways of aptamer-selection methods such as Acyclic Identification of Aptamers ("AIA") and SELEX, respectively. AIA, also called HTSA (High Throughput Screening of Aptamers) in co-pending PCT patent application PCT/US2009/037022 published as WO2009/151688, the entire content of which is incorporated herein by reference, is an acyclic procedure that distinguishes aptamers within libraries preferably having pre-defined secondary structures, where, on average, each sequence in the library is represented multiple times. These over-represented libraries have randomized regions of length, "m", where generally "m" is less than 26.

Acyclic identification cannot be applied to libraries that only have single copies of aptamer candidates, which is the general case for sparsely represented libraries often used in SELEX. As a means to obtain enriched representation (higher copy numbers) in a library that would enable the practice of AIA, the current invention describes methods and compositions for over-represented libraries with reduced complexity. Even with reduced complexity, libraries with "m" greater than 26 still span fruitful domains of the aptamer space.

The complexity of a library is related to the diversity of sequences in the library. The term "reduced complexity" in a daughter library (L2) refers to the removal of sequences from a parental library (L1) through a refinement or enrichment step. If L1 is very sparsely represented, it will contain zero copies of most possible sequences and single copies of the overwhelming majority of those sequences that are present. Thus, the L2 library with reduced complexity will contain fewer of the single copy sequences from L1. Neither L1 nor L2 is suitable for AIA-based aptamer identification. In a preferred embodiment, L2 is further amplified, e.g., by PCR, and the resulting L3 library will be over-represented, on average, with multiple copies of each sequence that is present after the L1-L2 complexity reduction. In general, the L3 library will have the same complexity as L2. With each sequence being over-represented, typically 100 to 10,000 copies, the L3 library is now amenable to AIA, as well as to SELEX. In a preferred embodiment, for every 100 pmol, an L3 library has, on average, at least about 3 or even higher (e.g., 5, 10, 100, 1000 or 10000) copies of each unique sequence.

Because the L2 and its offspring L3 library have been refined and enriched against the target, they yield less non-specific binding (noise) and provide more relevant hits and stronger signals in screening procedures for aptamer binding partners for the target. Therefore, the L2 and L3 libraries can be considered as having been "sensitized" or biased towards the target through the L1-L2 refinement step.

It is not necessary for L1 ("starting" library) or L2 ("intermediary" library) to be sparsely represented in order to practice the present invention. In one embodiment, L1 libraries can be over-represented as in the m=15 library of aptamer candidates with hairpin loops described in our WO2009/151688 patent publication or any over-represented library from m=3 to 26. Likewise, any library of pre-selected secondary structures with values of m from 3 to 26 can be used to practice the present invention whether the library is over or sparsely represented. In another embodiment, such libraries of pre-selected secondary structures are mixed prior to or after reduction of complexity.

In the simplest embodiments, complexity in L1 may be reduced by a preliminary round of refinement/enrichment against an individual target.

In a preferred embodiment, highly useful L2 libraries can be prepared by reducing the complexity of L1 libraries via one or more rounds of refinement against a plurality of substances similar to the target, including, but not limited to a target pool containing: (i) duplicates to thousands of proteins and polypeptides, (ii) duplicates to thousands, millions and even billions of peptides, small molecules, or polysaccharides, or (iii) of duplicates to a large but practical set of components from viruses, bacteria, cells, organisms or tissues from normal/healthy and/or diseased states. An example of such a pool with a large plurality of proteins is a cell lysate, which, in the case of *E. Coli* or yeast, may contain a few thousand proteins. Mammalian cell lysates may contain 20,000 or more proteins with many in modified forms, including isoforms, post-translational modifications, etc. Pools of peptides, small molecules, and polysaccharides can be prepared by direct synthesis using methods well known to chemists and biochemists. Pools of viruses, single-celled organisms can be mixed from stocks that are commercially available or in large collections, and cells from different tissues can be prepared by methods commonly used by biologists.

It is also not necessary to generate L2 libraries through refinement against all pooled substances, especially if some of the substances are incompatible with each other. In another embodiment, compatible pools can be used to generate several L2 libraries, and the L2 libraries, e.g., 10, 20, 50, 100 or even more of them, can be mixed afterwards into a comprehensive library before or after amplification.

An L3 library can be further refined against a plurality of targets to create libraries L4, L5, etc., which can also be mixed afterwards into a comprehensive library.

In the embodiment where lysates containing a large collection of proteins are used as target pools to refine L1 libraries into L2, it is likely that nearly all possible protein folds and epitopes for antibody recognition will be represented in the target pool. L3 libraries thus generated will be rich territories for aptamer discovery against nearly any target protein.

In one embodiment, L3 libraries generated against protein lysates from multiple organisms are combined to increase the diversity of protein folds and aptamer "epitopes" that the libraries of the present invention are sensitized to.

Over-represented L3 libraries generated against protein lysates can be used in the AIA (acyclic identification of aptamers) method to screen for aptamers against pools of duplicates to thousands of proteins. Subsequently, these aptamers can be individually synthesized and then matched to their partner protein by mass spectrometry, microarray, or other methodology known to identify the nature of a protein.

Similar library compositions and methods can be used for pools of other targets, such as peptides, small molecules, polysaccharides, components of viruses, bacteria, cells, organisms, or tissues from normal/healthy and diseased states.

The main purpose for preliminary refinement against a single target is to reduce the number of non-binding or weakly binding "noise" sequences, while preserving most of the higher affinity sequences for the target.

The main effect of preliminary refinement against a plurality of reagents similar to a target is to reduce the number of sequences unlikely to bind the target in a class of compounds, while preserving most of the higher affinity sequences for targets in the category of similar compounds.

Complexity may also be reduced by randomly removing sequences, e.g., by serial dilution of libraries beyond the point where only single copies exist for any individual sequence.

Reduced complexity libraries may also be generated by direct synthesis of sequences containing pre-selected structural features from known aptamers, with limited randomization in region(s) of the library sequences. These L1 will be fruitful domains of sequence space for aptamer discovery. These L1 libraries can be refined against pools of substances to generate new L2 and L3 libraries as described above.

In one aspect, the present invention provides a method for identifying an aptamer that binds to a target comprising the steps of:

(a) providing a starting library of a starting pool of aptamer candidates;

(b) reducing the sequence complexity of said starting library of aptamer candidates by a factor of at least about 100 to an intermediary pool of surviving aptamer candidates;

(c) amplifying said intermediary library of surviving aptamer candidates to an over-represented library of said surviving aptamer candidates such that, for every 100 pmol of said surviving aptamer candidates, each surviving aptamer candidate has, on average, at least about three copies;

(d) contacting said over-represented library with a target under a buffer condition that allows binding between members of said over-represented library and said target;

(e) isolating at least one aptamer candidate that is bound to said target; and (f) determining the sequence of said bound aptamer candidate.

In an embodiment, starting library in step (a) comprises at least $10^9$ distinct members. The starting library may be sparsely represented.

In an embodiment, step (b) comprises contacting said starting library with said target (or a plurality of distinct substances) under a buffer condition that allows binding between members of said starting library and said target, and then substantially reducing the number of unbound aptamer candidates from the starting pool of candidates. The plurality of distinct substances can be structural analogs of said target, and/or selected from the group consisting of proteins, peptides, small molecules, polysaccharides, bacterial components and viral components. In a particular embodiment, the plurality of distinct substances comprise parts or substantially the entire content of a cellular lysate.

In one feature, step (b) further comprises reducing the sequence complexity of said starting pool of aptamer candidates by a factor of at least about 1000 to said intermediary pool of surviving aptamer candidates.

In another feature, each of said aptamer candidates has a primary structure of substantially the same length and a pre-selected secondary structure, said primary structure comprising at least a variable nucleotide sequence where nucleotides at "m" number of positions are being varied, said secondary structure comprising at least a single-stranded region and a double-stranded region, wherein said variable sequence is at least part of said single-stranded region. The pre-selected secondary structure comprises a hairpin loop, a bulge loop, an internal loop, a multi-branch loop, a pseudoknot or combinations thereof.

In one feature, said primary structure of each aptamer candidate is substantially similar to a template aptamer, e.g., that has been previously provided through SELEX.

In one feature, step (e) further comprises ranking target-binding affinity of a plurality of bound aptamer candidates. In another feature, step (f) is accomplished through high throughput sequencing technology.

In another aspect, the present invention provides a method for identifying an aptamer that binds to a target comprising the steps of:

(a) providing a starting library of a starting pool of aptamer candidates;

(b) reducing the sequence complexity of said starting pool of aptamer candidates by a factor of at least about 100 to an intermediary library of surviving aptamer candidates;

(c) amplifying said intermediary library of surviving aptamer candidates to an over-represented library of said surviving aptamer candidates such that, for every 100 pmol of said surviving aptamer candidates, each surviving aptamer candidate has, on average, at least about three copies;

(d) contacting said over-represented library with a plurality of distinct targets under a buffer condition that allows binding between members of said over-represented library and said plurality of distinct targets;

(e) isolating at least one aptamer candidate that is bound to at least one of said plurality of distinct targets; and (f) determining the sequence of said bound aptamer candidate.

In one feature, there are at least 5 of said plurality of distinct targets in step (d).

In a further aspect, the present invention provides a method for identifying an aptamer that binds to a target comprising the steps of:

(a) providing a plurality of starting libraries each comprising a starting pool of aptamer candidates, each of said aptamer candidates of substantially the same length while having a primary structure and at least one common pre-selected secondary structure, said primary structure comprising at least a variable nucleotide sequence where nucleotides at m number of positions are being varied, said common pre-selected secondary structure varying among said plurality of starting libraries;

(b) reducing the sequence complexity in each of said plurality of starting starting libraries by a factor of at least about 100 to a plurality of intermediary libraries of surviving aptamer candidates;

(c) amplifying each of said plurality of intermediary libraries to a plurality of over-represented libraries of said surviving aptamer candidates such that, for every 100 pmol of said surviving aptamer candidates, each surviving aptamer candidate has, on average, at least about three copies;

(d) mixing said plurality of over-represented libraries into a comprehensive library with surviving aptamer candidates of varying secondary structures;

(e) contacting said comprehensive library with a target under a buffer condition that allows binding between members of said comprehensive library and said target;

(f) isolating at least one aptamer candidate that is bound to said target; and (g) determining the sequence of said bound aptamer candidate.

In yet another aspect, the present invention provides an aptamer library biased towards multiple pre-selected targets, comprising an over-represented library of aptamer candidates produced by amplifying a sparsely represented library such that each aptamer candidate has, on average, at least about three copies for every 100 pmol of said aptamer candidates, said sparsely represented having been reduced of its sequence complexity through at least one round of refinement against at least about ten pre-selected targets. The pre-selected targets may comprise structurally related analogs. In an embodiment, said pre-selected targets comprise parts or substantially the entire content of a cellular lysate.

It should be understood that this application is not limited to the embodiments disclosed in this Summary, and it is intended to cover modifications and variations that are within the scope of those of sufficient skill in the field, and as defined by the claims.

DETAILED DESCRIPTION

Figure 1:
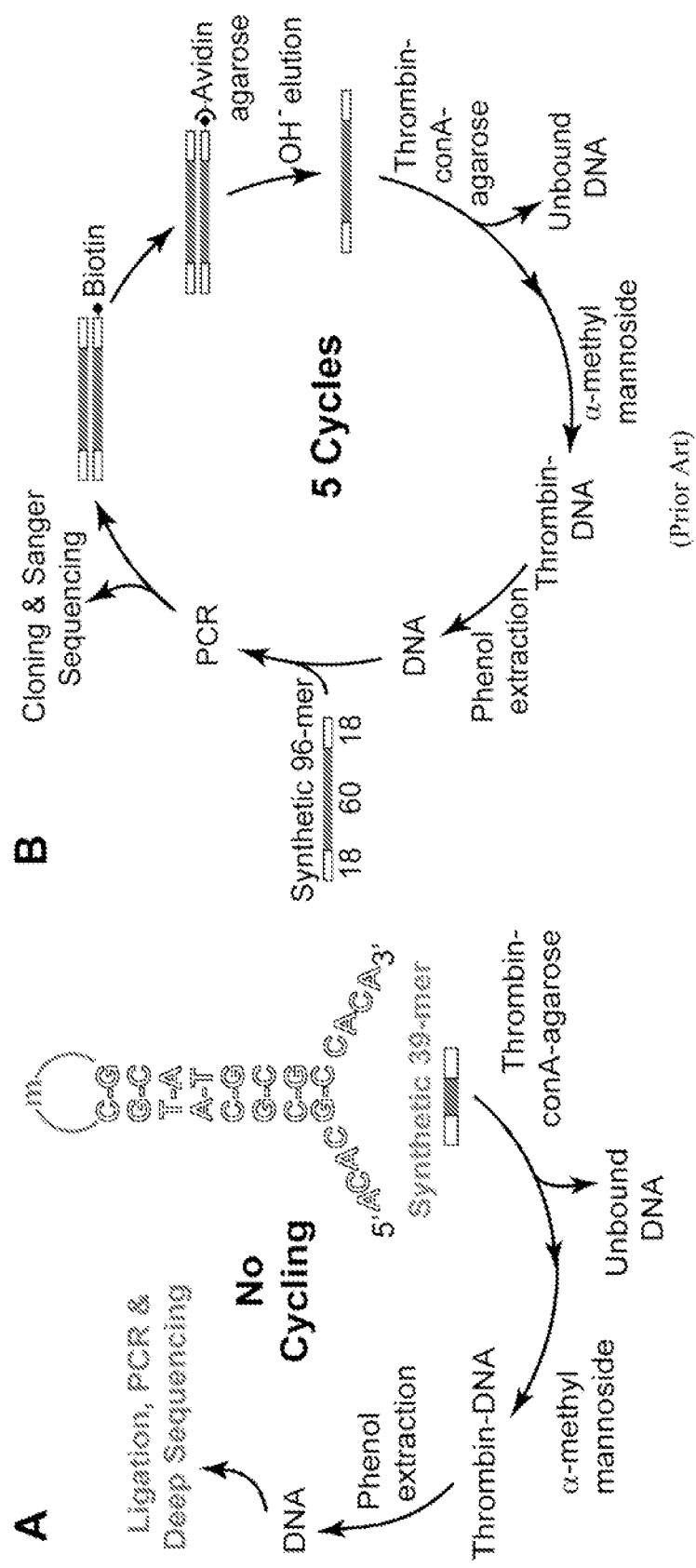
FIG. 1 depicts a thrombin-specific aptamer identification protocol (A) using the AIA procedure and (B) using a prior procedure as described in Bock et al., *Nature* 355: 564-566 (1992). The synthetic 39-mer in the libraries depicted in (A) shows a stem-hairpin loop as its secondary structure. The primary sequence (SEQ ID NO:1) shows a variable sequence region in the loop region.

Unless defined otherwise, all technical and scientific terms used herein have the same meaning as is commonly understood by one of skill in the art. The following definitions are provided to help interpret the disclosure and claims of this application. In the event a definition in this section is not consistent with definitions elsewhere, the definition set forth in this section will control.

As used herein, the term "about" or "approximately" or the symbol "~" or "≅" when used in conjunction with a number refers to any number within 5, 10 or 15% of the referenced number.

The term "plurality", as used herein, refers to a quantity of two or more.

As used herein, "nucleic acid," "oligonucleotide," and "polynucleotide" are used interchangeably to refer to a polymer of nucleotides of any length, and such nucleotides may include deoxyribonucleotides, ribonucleotides, and/or analogs or chemically modified deoxyribonucleotides or ribonucleotides. The terms "polynucleotide," "oligonucleotide," and "nucleic acid" include double- or single-stranded molecules as well as triple-helical molecules. An oligonucleotide may have any number of nucleotides theoretically but preferably 2-200 nucleotides, more preferably 10-100 nucleotides, and yet more preferably 20-80 nucleotides.

As used herein, "target molecule" and "target" are used interchangeably to refer to any molecule to which an aptamer can bind. "Target molecules" or "targets" refer to, for example, proteins, polypeptides, nucleic acids, carbohydrates, lipids, polysaccharides, glycoproteins, hormones, receptors, antigens, antibodies, affybodies, antibody mimics, viruses, pathogens, toxic substances, substrates, metabolites, transition state analogs, cofactors, inhibitors, drugs, small molecules, dyes, nutrients, pollutants, growth factors, cells, tissues, or microorganisms and any fragment or portion of any of the foregoing. In one embodiment, a "target" refers to a cell surface molecule, such as a cell membrane protein.

As used herein, "sequence" and nucleic acid "molecule" are used interchangeably. Thus a pool of $10^{14}$ RNA sequences means the same as a pool of $10^{14}$ RNA molecules.

As used herein, "aptamers" that bind targets and other members of a pool of oligonucleotides are typically comprised of DNA, RNA, PNA, nucleotide analogs, modified nucleotides or mixtures of any of the above. Aptamers and other pool members in a library may be naturally occurring or made by synthetic or recombinant means. Aptamers and pool members used herein comprise single stranded regions and regions of secondary structure including, but not limited to, a hairpin loop, a bulge loop, an internal loop, a multi-branch loop, a pseudoknot or combinations thereof. Aptamers and pool members may comprise naturally occurring nucleotides, nucleotides that have been modified in some way, such as by chemical modification, and unnatural bases, for example 2-aminopurine. Aptamers and pool members may be chemically modified, for example, by the addition of a label, such as a fluorophore, or a by the addition of a molecule that allows the aptamer to be crosslinked to a molecule to which it is bound. Aptamers or aptamer candidates are of the same "type" if they have similar sequences or are capable of specific binding to the same target molecule. The length of aptamers and pool members will vary, but it is preferably less than about 100 nucleotides.

An "aptamer" or "aptamer candidate" may have a low, moderate or high binding affinity for a target molecule. It is recognized that affinity interactions are a matter of degree; however, in this context, the "specific binding affinity" of an aptamer for its target means that the aptamer binds to its target generally with a much higher degree of affinity than it binds to other components in a test sample.

As used herein, "a template aptamer" is an aptamer having an affinity for a target that can be improved, i.e., modification of the nucleotide sequence of an aptamer to increase or decrease the affinity of the template aptamer for the target. In one embodiment, "a template aptamer" is a SELEX-derived aptamer.

As used herein, "high affinity" binding refers to binding of a candidate aptamer to a target with binding dissociation constant $K_d$ is less than 100 nanomolar (100 nM).

As used herein, "moderate affinity" binding refers to binding of a candidate aptamer to a target with binding dissociation constant $K_d$ from 0.1 micromolar to 100 micromolar (0.1 μM to 100 μM).

As used herein, "low affinity" binding refers to binding of a candidate aptamer to a target with binding dissociation constant $K_d$ from 0.1 millimolar to 1000 millimolar (0.1 mM to 1000 mM).

As used herein, the term "library" refers to a plurality of compounds; a library may also be referred to as a "pool."

As used herein, the term "small molecules" and analogous terms include, but are not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) having a molecular weight less than about 10,000 grams per mole. In some embodiments, the term refers to organic or inorganic compounds having a molecular weight less than about 5,000 grams per mole, less than about 1,000 grams per mole, less than about 500 grams per mole, less than about 100 grams per mole. Salts, esters, and other pharmaceutically acceptable forms of such compounds are also encompassed.

As used herein, primary structure of an oligonucleotide refers to its nucleotide sequence.

As used herein, "secondary structures" of an oligonucleotide refer to RNA or DNA secondary structures including, but is not limited to, a hairpin loop, a bulge loop, an internal loop, a multi-branch loop, a pseudoknot or combinations thereof.

"Pre-selected secondary structures" refers to those secondary structures that are engineered into an aptamer library by design.

As used herein, a "variable sequence" or a "variable nucleotide sequence" refers to a base sequence within an aptamer that includes at least one enumerated or randomized position. In some embodiments, "a variable sequence" also includes invariant nucleotides where the nucleotide sequence at that location is the same amongst all members of a given population of aptamers, as long as there is at least one other base that is not constant. In one embodiment, a variable sequence is confined to a single-stranded region of an aptamer. In another embodiment, a variable sequence comprises nucleotides at positions in the double-stranded region and are no more than three nucleotides away from an end of the single-stranded region. The total number, m, of varied bases is often specified.

A "double-stranded region" refers to a region of an aptamer where two single stranded regions have sufficient complementarity to base-pair with each other. In some embodiments, the inclusion of randomized sequences within a region originally intended as single-stranded may permit varied stem positions because randomized positions may be able to base pair with each other thus extending the double-stranded region into a previously single stranded region. In other words, the "single stranded" region of some candidate aptamers may include varied loop positions that may adopt structures with Watson-Crick or non-canonical pairs, triples, quadruples.

As used herein, the term "stringency" is used in reference to the conditions of temperature, ionic strength, and the presence of other compounds such as organic solvents, under which binding assays are conducted.

As used herein, the term "average representation," for a nucleic acid pool, means the statistical average of the number of copies for each distinct sequence, which is the total number of sequence molecules that physically exist in the pool divided by the number of distinct sequences, i.e., sequences distinguishable in nature, that are possible. Average representation is given herein by the symbol, R.

As used herein, the term "full representation" for a nucleic acid pool means that the average representation is large enough that all possible base sequences within the given perimeters of the library, e.g., with a pre-selected total length for each member nucleic acid and/or length of the variable sequence region, are present in the pool.

As used herein, the term "sparse representation" "sparsely represented" and other derivative terms mean that fewer than all possible sequences, given the perimeters on length and composition of the variable region, are present in a library.

Typical libraries used in the past for aptamer discovery represent a tiny fraction of all possible distinct sequences, e.g., $R=10^{-8}$.

As used herein, the term "over-representation" or "ample representation" and their derivative terms mean that each distinct sequence that is present in the library has on average at least three ($R=3$), and preferably more than three copies in a library ($R>3$).

As used herein, the term "complexity" refers to the diversity of distinct base sequences in a library. For instance, a library with a total of $10^{14}$ sequences where each distinct sequence is represented one time only is more complex than a library with a total $10^{14}$ sequences where each unique sequence is represented 1,000 times. As used herein, the term "reduced complexity" referring to a daughter library (L2) means that distinct sequences have been removed from a parental library (L1). After amplification of L2 by PCR, the resulting library, L3, will be over-represented with multiple copies of each sequence that was present in L2, but will have the same complexity as L2 within the limits of equal amplification efficiencies for all distinct sequences in L2.

Acyclic Identification of Aptamers (AIA)

AIA may be applied to find aptamers against a variety of targets including, but not limited to, proteins, peptides, small molecules, polysaccharides, or other classes of molecules, various types of organisms such as viruses, microorganisms, and cells from different categories of normal and diseased tissues.

AIA can be practiced where the aptamer library is provided in a solution where it binds to a target or a plurality of targets, and aptamer-target complexes are separated or otherwise partitioned from unbound or weakly bound sequences. Separation techniques include, but are not limited to, immobilization on a solid support, affinity chromatography, gel filtration, electrophoretic mobility shift, capillary electrophoresis, gel filtration or other techniques known to those skilled in the art of molecular biology. The bound aptamers are then ligated with adaptor sequences, and PCR amplified prior to high-throughput sequencing; a step may be included to remove the target from the target-aptamer complex or from the ligated aptamers. The identity of target-bound aptamers is determined by sequencing, and aptamer affinities are initially ranked by the number of times each is counted. These procedures are described in further detail in our WO2009/151688 patent publication.

Secondary screens are used for more accurate quantification of affinity, as by surface plasmon resonance (SPR), electrophoretic mobility shift assays (EMSA), microarrays, or another method known to those skilled in the art of measuring the affinity of nucleic acids for targets, including proteins, small molecules, polysaccharides, or other classes of molecules, and various types of organisms such as viruses, microorganisms, cells, and different categories of normal and diseased tissues.

In vitro evolution (Ellington A D, et al., *Nature* 346: 818-822(1990); Marshall K A, et al., *Methods Enzymol* 318: 193-214 (2000)), often called SELEX (Tuerk C, et al., *Science* 249: 505-510 (1990); Fitzwater T, et al., *Methods Enzymol* 267: 275-301 (1996)), has been the standard method for aptamer discovery. SELEX (Gold L, et al. *Annu Rev Biochem* 64: 763-797(1995)), compared to our acyclic protocol in FIG. 1A, typically uses five to fifteen cycles of target-partitioning and amplification to enrich aptamer candidates from a pool containing randomized segments of length, m, where m≥30 is typical (FIG. 1B). Typical starting libraries for SELEX have oligomers with central randomized regions (30-70 nt) flanked by fixed regions needed for amplification and cloning (overall length often ≥90 nt). This is illustrated in FIG. 1B in a procedure that screens for an aptamer that binds human α-thrombin, where the aptamer core sequence is only 15 bases, as originally deduced by Bock et al., *Nature* 355: 564-566 (1992). The authors used five SELEX cycles, starting with 100 pmol of a 96 mer DNA library with a 60 nt randomized region. Most possible sequences are not represented in naïve (unpartitioned) SELEX pools, e.g., in 100 pmol of a pool with m=60, the probability is only $5\times10^{-23}$ that a particular 60 mer segment is present (see Table 1). Thus, virtually all of the $6\times10^{13}$ molecules in the pool occur as single copies. Despite this sparse representation, high affinity molecules that do exist come to dominate the evolving pool under the selective pressure of binding where repeated motifs identify aptamers in the final pool.

Our WO2009/151688 patent publication discloses AIA via the application of high-throughput sequencing to over-represented libraries to distinguish aptamers after a single partitioning step. Over-represented libraries were disclosed that are designed with secondary structural motifs that are known to be rich territories for aptamer discovery, as in hairpin loops (FIG. 1A). Only fairly short randomized regions are required for acyclic identification as described in the WO2009/151688 patent publication, where typically m<25, when the full complement of A, C, G, T(U) occurs at each randomized position. The use of such structured libraries usually avoids the necessity for truncating aptamer candidates to discover a core binding sequence.

Illustration of Acyclic Identification of Aptamers that Bind Human Alpha-Thrombin and Carbohydrates.

Referring now to FIG. 1A, thrombin was chosen as a target to validate the acyclic protocol in AIA and described in detail in our WO2009/151688 patent publication. The canonical DNA aptamer (GG TT GG TGT GG TT GG described by Bock et al., which is coded herein as "Thb1", SEQ ID NO:4) and lower affinity relatives were found within a naïve library that substantially over-represents each possible sequence. This library was also adapted to the sequencing platform used (Illumina Genome Analyzer IIx) with short read lengths, but any high throughput DNA sequencer could be used. A natural result of the investigation was that all possible thrombin binding sequences within the sequence space encompassed by the m=15 library were evaluated. The acyclic protocol (AIA) reduced the sample manipulations by a factor of six compared to Bock et al. and required only standard methods in molecular biology coupled with high-throughput sequencing that is now widely available.

The fifty top-ranked aptamers that were found in an AIA experiment using the experimental conditions reported by Bock et al. are shown on the left in Table 2. The leading aptamer was Thb1, which was counted 46,444 times. The same experiment also found aptamers that bind to sugars, including glucose and alpha-methyl mannoside, which were present in the solutions used to store concanavalin A beads used for immobilization of thrombin. These aptamers are shown at the right of Table 2. The leading candidate is GCTATCATCGCAACG coded herein as "Carb1", (SEQ ID NO:54), which was counted 29,405 times, and ranked second only to Thb1. Carb1 has Kd=520 nanomolar for alpha-methyl-mannoside (AMM), and 1.4 micromolar for glucose as determined by surface plasmon resonance imaging. The affinity for AMM ranks Carb1 in the top third of aptamers for small molecules. The co-isolation of these aptamers in a single experiment validates AIA in general. It further illustrates that the evolution-free AIA procedure is capable of the parallel isolation of aptamers for different targets (thrombin and sugars), and simultaneously identifies high-affinity (high counts) and low-affinity aptamers for each target.

Applications of Present Invention in AIA

As discussed below in connection with Table 1, in the above example of AIA where a library of aptamer candidates with a variable sequence region of 15 nt are used to screen for a binding partner for thrombin, the starting library was amply or over-represented. However, this ceases to be the case at higher values of m. In situations where m equals or is larger than 22, the starting library will be sparsely represented, which would not allow the use of AIA. We now go over the reasons in detail with the aid of Table 1.

TABLE 1

Representation of sequences in naïve pools.

|   | B | 4 | 4 |
|---|---|---|---|
|   | H | 5.0E+06 | 5.0E+06 |
|   | # nmol | 0.1 | 25 |
|   | A | 6.0E+13 | 1.5E+16 |
| m | U | R (0.1) | R (25) |
| 1 | 4.0E+00 | 1.5E+13 | 3.8E+15 |
| 2 | 1.6E+01 | 3.8E+12 | 9.4E+14 |
| 3 | 6.4E+01 | 9.4E+11 | 2.4E+14 |
| 4 | 2.6E+02 | 2.4E+11 | 5.9E+13 |
| 5 | 1.0E+03 | 5.9E+10 | 1.5E+13 |
| 6 | 4.1E+03 | 1.5E+10 | 3.7E+12 |
| 7 | 1.6E+04 | 3.7E+09 | 9.2E+11 |
| 8 | 6.6E+04 | 9.2E+08 | 2.3E+11 |
| 9 | 2.6E+05 | 2.3E+08 | 5.7E+10 |
| 10 | 1.0E+06 | 5.7E+07 | 1.4E+10 |
| 11 | 4.2E+06 | 1.4E+07 | 3.6E+09 |
| 12 | 1.7E+07 | 3.6E+06 | 9.0E+08 |
| 13 | 6.7E+07 | 9.0E+05 | 2.2E+08 |
| 14 | 2.7E+08 | 2.2E+05 | 5.6E+07 |
| 15 | 1.1E+09 | 5.6E+04 | 1.4E+07 |
| 16 | 4.3E+09 | 1.4E+04 | 3.5E+06 |
| 17 | 1.7E+10 | 3.5E+03 | 8.8E+05 |
| 18 | 6.9E+10 | 8.8E+02 | 2.2E+05 |
| 19 | 2.7E+11 | 2.2E+02 | 5.5E+04 |
| 20 | 1.1E+12 | 5.5E+01 | 1.4E+04 |

TABLE 1-continued

Representation of sequences in naïve pools.

| 21 | 4.4E+12 | 1.4E+01 | 3.4E+03 |
|---|---|---|---|
| 22 | 1.8E+13 | 3.4E+00 | 8.6E+02 |
| 23 | 7.0E+13 | 8.6E-01 | 2.1E+02 |
| 24 | 2.8E+14 | 2.1E-01 | 5.3E+01 |
| 25 | 1.1E+15 | 5.3E-02 | 1.3E+01 |
| 26 | 4.5E+15 | 1.3E-02 | 3.3E+00 |
| 27 | 1.8E+16 | 3.3E-03 | 8.4E-01 |
| 28 | 7.2E+16 | 8.4E-04 | 2.1E-01 |
| 29 | 2.9E+17 | 2.1E-04 | 5.2E-02 |
| 30 | 1.2E+18 | 5.2E-05 | 1.3E-02 |
| 35 | 1.2E+21 | 5.1E-08 | 1.3E-05 |
| 40 | 1.2E+24 | 5.0E-11 | 1.2E-08 |
| 60 | 1.3E+36 | 4.5E-23 | 1.1E-20 |

Boxed: Beyond Diversity Limit
Beyond Synthesizer Limit for 1 umol scale synthesis A = the number of all strands in the pool.
m = length of randomized sequence.
B = number of varied bases at each position (usually 4).
H is the number of readable sequences from a flow cell.
U = $B^m$, the number of possible unique sequences of length, m.
R = A/U, the average representation of each unique molecule in a pool.

TABLE 2

Fifty top-ranked aptamers for human alpha-thrombin and for carbohydrates.

| SEQ ID NO: | Thrombin Aptamer DNA sequence | Counts | SEQ ID NO: | Carbohydrate Aptamer DNA sequence | Counts |
|---|---|---|---|---|---|
| 4 | GGTTGGTGTGGTTGG | 46444 | 54 | GCTATCATCGCAACG | 29405 |
| 5 | GGTTGGTGTGGTTTG | 2451 | 55 | GCTATCATCGCCACG | 1040 |
| 6 | GGTTGGTGTTGTTGG | 647 | 56 | GCTATCATCGCACCG | 678 |
| 7 | GGTTGGTGTGGTTGT | 591 | 57 | GCTCTCATCGCAACG | 354 |
| 8 | GGTTGGTTTGGTTGG | 419 | 58 | GCTATCATCGCAACC | 220 |
| 9 | GGCTGGTGTGGTTGG | 255 | 59 | GCTATCCTCGCAACG | 199 |
| 10 | GGTTGGTGTGTTTGG | 215 | 60 | GCTATCATCGCAAAG | 160 |
| 11 | GGTTGGCGTGGTTGG | 195 | 61 | GCTATCATCCCAACG | 153 |
| 12 | GGTTGGTGTTGTTTG | 159 | 62 | GCTATTATCGCAACG | 103 |
| 13 | GGTTGGTGTGGCTGG | 125 | 63 | GCTCTCATCGCCACG | 95 |
| 14 | GGTTTGTGTGGTTGG | 124 | 64 | GCTATCATCGCAATG | 91 |
| 15 | GGTTGGTGTGGTTTT | 124 | 65 | GCTATCATCTCAACG | 80 |
| 16 | GGTTGTTGTGGTTGG | 114 | 66 | GCTACCATCGCAACG | 79 |
| 17 | GGTTGGGGTGGTTGG | 105 | 67 | GCCATCATCGCAACG | 77 |

TABLE 2-continued

Fifty top-ranked aptamers for human alpha-thrombin and for carbohydrates.

| SEQ ID NO: | Thrombin Aptamer DNA sequence | Counts | SEQ ID NO: | Carbohydrate Aptamer DNA sequence | Counts |
|---|---|---|---|---|---|
| 18 | GGTTGGTGCGGTTGG | 97 | 68 | GCTATCATCGCTACG | 76 |
| 19 | GGTTGGTGTGGTCGG | 94 | 69 | GCTTTCATCGCAACG | 69 |
| 20 | GGTCGGTGTGGTTGG | 90 | 70 | GCTATCATTGCAACG | 68 |
| 21 | GGGTGGTGTGGTTGG | 90 | 71 | GCTATCATCGCAACT | 67 |
| 22 | GGTTGGTGTGGTTGC | 90 | 72 | GCTATCACCGCAACG | 67 |
| 23 | GGTTGGTTTGGTTTG | 87 | 73 | GCTATCATCGCCCCG | 66 |
| 24 | GGTTGGTCTGGTTGG | 81 | 74 | GCTATCATCGCATCG | 66 |
| 25 | GGTTGGTGTGGGTGG | 74 | 75 | GCTATCATAGCAACG | 65 |
| 26 | GGTTGGTGTCGTTGG | 70 | 76 | GATATCATCGCAACG | 56 |
| 27 | GGTTCGTGTGGTTGG | 70 | 77 | GCTCTCATCGCACCG | 54 |
| 28 | GGTTGGTGTGGTTCG | 68 | 78 | GCTATCATCGAAACG | 53 |
| 29 | CGTTGGTGTGGTTGG | 60 | 79 | GCTATCATCGGAACG | 53 |
| 30 | GGTTGCTGTGGTTGG | 57 | 80 | GCTATCCTCGCACCG | 48 |
| 31 | GCTTGGTGTGGTTGG | 54 | 81 | GCTATCTTCGCAACG | 44 |
| 32 | GGTTGGTGTTGTTGT | 53 | 82 | GCTATCATCGTAACG | 42 |
| 33 | GGTTGGTGTGCTTGG | 47 | 83 | ACTATCATCGCAACG | 42 |
| 34 | AGTTGGTGTGGTTGG | 43 | 84 | GCTATAATCGCAACG | 37 |
| 35 | GGTTGGTGTGTTTTG | 40 | 85 | CCTATCATCGCAACG | 35 |
| 36 | GGTTGGTGGGGTTGG | 39 | 86 | GCTATCATCCCAACC | 34 |
| 37 | GGTTGGAGTGGTTGG | 34 | 87 | GCTATCATCACAACG | 33 |
| 38 | GGTTGGTATGGTTGG | 33 | 88 | GCTATCATCGCAAGG | 32 |
| 39 | GGTTGGTGTTGTTTT | 26 | 89 | GCTATCATCGCAACA | 30 |
| 40 | GGTTGGTTTTGTTGG | 23 | 90 | GTTATCATCGCAACG | 30 |
| 41 | GGTGGGTGTGGTTGG | 23 | 91 | GCTATCATCGCACAG | 24 |
| 42 | TGTTGGTGTGGTTGG | 22 | 92 | GCTGTCATCGCAACG | 22 |
| 43 | GGTTGGTGTAGTTGG | 22 | 93 | GCTATCATCGCAAAC | 21 |
| 44 | GGATGGTGTGGTTGG | 21 | 94 | GCTCTCATCGCCCCG | 21 |
| 45 | GGTTAGTGTGGTTGG | 21 | 95 | GCTATCATCGCCACC | 20 |
| 46 | GGTTGGTGTGGTTAG | 21 | 96 | GCTATCATCGCGACG | 18 |
| 47 | GGTTGGTGAGGTTGG | 20 | 97 | GGTATCATCGCAACG | 17 |
| 48 | GGTTGGTGTGATTGG | 20 | 98 | GCTAGCATCGCAACG | 17 |
| 49 | GGTTGGTGTGTTTGT | 20 | 99 | TCTATCATCGCAACG | 16 |
| 50 | GGTTGGTGTGGATGG | 19 | 100 | GCTATCATCCCCACG | 15 |
| 51 | GGTTTGTGTGGTTTG | 19 | 101 | GCGATCATCGCAACG | 15 |
| 52 | GATTGGTGTGGTTGG | 18 | 102 | GCTATCATCGCACCC | 14 |
| 53 | GGTTGGTGTGGTTGA | 17 | 103 | GCTATCATCGACACG | 13 |

Each 15-nucleotide sequence listed above in Table 2 had a 5'-flanking sequence (F5), ACACGCGCATGC (SEQ ID NO:2), and a 3'-flanking sequence (F3), GCATGCGCCACA (SEQ ID NO:3). There were a total of 1,959,748 "qualified" sequencing reads from the Illumina GA IIx that had (1) the F5 sequence with two, one or zero substitutions, deletions or insertions, (2) the first five bases of F3 with one or zero substitutions, deletions or insertions, and (3) exactly 15 bases in the randomized region. Among the qualified reads there were 1,728,220 unique sequences of which 1,598,788 were counted one time only.

Representation.

In the present disclosure, we describe the occurrence of distinct sequences within an aptamer library with the concept of average representation, R. In previous disclosures including our WO2009/151688 patent publication, we have also used the term "sampling" to describe the occurrence of distinct sequences within an aptamer library. However, in the present disclosure, the term "sampling" refers to the action of taking a physical sample for sequencing.

The number of possible distinct sequences, U, in a pool with m randomized nucleotides is $4^m$ when four nucleotides occur at each randomized position in equal population. Therefore, the average representation of a distinct sequence can be calculated if one divides a given amount of the nucleic acid molecules (A) in the library by U:

$$R=A/U.$$

Referring now to Table 1, for the $6\times10^{13}$ molecules in 100 pmol (0.1 nmol) of a library with m=15, U is 1.1 billion distinct sequences; R is thus 56,000 for each of these sequences, making this an over-represented library. For a library with m=22 and R=3.4, R is the average taken over a distribution of discrete objects. Thus, the peak in the distribution of the number for each distinct sequence in this library occurs at three copies, while nearly as many distinct sequences occur in four copies. Such a random distribution of 18 trillion distinct sequences in a total of 60 trillion sequence molecules will have some distinct sequences present in two and five copies, as well as other multiples. Poisson statistics can be used here to predict that there will be some distinct sequences present in zero copies—absent from the distribution. Accordingly, when m=22, the library is considered to be just beyond the diversity limit for 100 pmol of the library content when full representation of all distinct sequences is unlikely. By contrast, Poisson statistics predict that for m=21 (R=14), the overwhelming majority of possible distinct sequences are present in the library. The original pool of Bock et al. Nature 355: 564-566 (1992) had $R=5\times10^{-23}$ (m=60); and thus, was very sparsely represented. In such a pool (whenever R<<1), it is extremely unlikely for any sequence to occur in more than one copy.

At a pool size of 25 nmol (last column in Table 1), when m reaches 26 or larger, the library is beyond the diversity limit. It is common to perform library synthesis on the 1,000 nmol scale, so acyclic aptamer discovery with m=25 should be practical if a sufficient amount of the target is available. However, the synthesizer limit is passed at m=30 for a 1,000 nmol synthesis. That is, $U=1.2\times10^{18}$ and fewer molecules will be produced from synthesis at this scale (<$6\times10^{12}$). While it is possible to increase the synthesis scale, it may become prohibitively expensive to supply enough target molecules for acyclic identification.

In sum, for 100 pmol (0.1 nmol) of aptamer candidates, the library is no longer amply represented, i.e., is sparsely represented, when m≥22. For 25 nmol of aptamer candidates, the library is no longer amply represented, i.e., is sparsely represented, when m≥26. The AIA methodology ceases to work in sparsely represented libraries, so the libraries have to be enriched somehow. To that end, the present invention provides the solution that not only enriches the library but also bias it towards yielding binding partners for the target with higher specificity.

Sampling.

A primary advantage of using high-throughput sequencing in aptamer discovery is that many more sequences are sampled in the partitioned pool than when Sanger sequencing is utilized. We define the Sampling Ratio, SR, as the ratio of total qualified reads to the total number of sequences in the pool. This is the fraction that was physically sampled; in the work presented here SR is taken as the fraction of the partitioned pool that was sampled.

Bock et al. reported 0.01% recovery of DNA from the 100 pmol applied to thrombin immobilized on ConA-agarose beads in the first cycle of SELEX (determined using $^{32}$P-labeled DNA). Thus, about $6\times10^9$ sequences survived partitioning from the initial pool of $6\times10^{13}$. As described above, the overwhelming majority of m=60 sequences in the initial pool were present as single copies. If Bock et al. had sequenced 32 clones following cycle 1 (as they did after cycle 5) SR would have been $32/6\times10^9=5\times10^{-9}$, sampling one molecule per 200 million.

By contrast, the experiments reported in our WO2009/151688 patent publication have a much higher value for SR. Assuming that partitioning has the same efficiency as for Bock et al., and for 2 million qualified GA reads, $SR=2\times10^6/6\times10^9=3\times10^{-4}$: then about 1 molecule was sampled per 3,000 recovered after partitioning (qualified reads have proper fixed sequences flanking the variable region).

Signal to Noise.

The counts for authentic aptamers are regarded as the signal in our experiment. We have shown that the signal is strongly correlated with binding affinity in WO2009/151688. If the partitioning step is efficient, the signal for Thb1 should be proportional to the number of Thb1 sequences in the naïve pool. Relatives of Thb1 will have signals reduced by their less efficient retention by the Thb protein in partitioning. The same should hold for Carb1 and its relatives (see Table 2). Carb1 is the second-highest ranked aptamer found after Thb1, and was found to bind carbohydrates, including glucose and alpha-methyl mannoside (AMM). On the other hand, random noise should arise primarily from sequences that are accidentally carried forward in the partitioning step. Most signal sequences will be correlated to Thb1, while noise sequences should be uncorrelated to Thb1 and each other. That is, each noise sequence has a tiny probability for occurrence. For m=15, a noise sequence that does not bind a target has one chance in 1.1 billion of being chosen at random (see value of U in Table 1 for m=15). A second noise sequence would be randomly selected from the 1.1 billion, and so on, for all 1.7 million "noise" sequences counted one time only (see note to Table 2). A sequence clustering algorithm, such as ClustalX would not be expected to find a significant correlation among 1,000 such noise sequences.

The noise threshold is due to multiples of non-binding sequences that must be expected for molecules that are sampled randomly from the partitioned pool. As discussed under Sampling, above, there should be about $6\times10^9$ total sequences in this pool, not all distinct because U $1.1\times10^9$ (Table 1). This distribution is skewed toward sequences having some affinity for the target. The skewness is small as only ~2% of the sample contains signal sequences. At $SR=3\times10^{-4}$, the $2\times10^6$ qualified reads must contain some multiples of noise sequences, and the noise threshold can be estimated at a count of ~3 using Poisson statistics (see WO2009/151688), and at 4 to 5 where significant numbers of noise sequences become apparent by their lack of correlation with Thb1 or Carb1 in analyses using ClustalX. (In this analysis, both signal and noise sequences are assumed to be amplified equally by PCR prior to clustering on the GA flow cell. Although PCR may be biased against particular sequences or structural motifs, it is unlikely to strongly alter the distribution of millions of non-binding noise sequences that pass through a purification process by random chance. Neither is it likely to distort the distribution of signal sequences for the Thb1 family, as the counts have been shown to correlate with affinity for thrombin in WO2009/151688.)

We conclude that the signal/noise ratio in our thrombin-experiment was very high, specifically, $S/N \cong 10,000$ (46,444 divided by 4 or 5).

Over-Representation Limit.

It has been shown above that acyclic identification of aptamers (AIA) provides robust results for 100 pmol of over-represented libraries with m=15 (R=56,000). Due to Poisson noise, the value of S/N value must tend toward one before R is reduced to one. Distinguishing aptamers by counting after acyclic identification cannot succeed when S/N=1, and must instead rely on motif recognition and/or cyclic enrichment. However, at $S/N \cong 10,000$ for a 100 pmol pool with m=15, it is certain that acyclic identification can be achieved at larger values of m and for larger pool sizes.

There is, however, a practical lower limit on R even for over-represented libraries. This limit occurs when the value of S/N approaches one, and acyclic identification cannot be used to distinguish aptamers. It is unlikely that acyclic identification can succeed for 100 pmol of pool and m=22 (where R=3.4, see Table 1, column 3), or at 25 nmol of pool and m=26 (where R=3.3, Table 1, column 4). A more practical limit, given current sequencing technology, is to use pools with $R \cong 200$ (100 pmol, m=19 or 15 nmol, m=23, Table 1); this would reduce the signal 300-fold for an aptamer requiring the full diversity of m sites, giving $S/N \cong 40$ assuming that the experiment scales according to our thrombin results. There is reason to expect a lower noise threshold from these more diverse libraries. Thai is because the Poisson distribution predicts that fewer multiples of sequences will occur in these larger libraries, so fewer multiples will be randomly carried forward by partitioning. Therefore, the background could be lower than the estimate of four to five counts used above.

Comparison of Acyclic Identification with SELEX

The acronym, SELEX, is derived from the term, Systematic Evolution of Ligands by Exponential enrichment. Prominent is the word "evolution." We have described an acyclic procedure for distinguishing DNA sequences with high affinity for targets such as proteins or small molecules that does not rely on cyclic evolution.

The variable region within a library of $10^{14}$ molecules with a large value of m will contain all possible sub-sequences below a certain threshold length. For instance, it is easy to see that even a sparsely represented library will contain all possible dinucleotide and trinucleotide sequences. According to Table 1, the threshold is ~22 nt for 100 pmol of library. This has been used to argue that complete representation is unnecessary. See Marshall K A, et al. *Methods Enzymol* 318: 193-214 (2000). However, when each sequence is present only once in a sparsely represented library, cyclic enrichment is mandatory before an aptamer can be distinguished by counting. It would be difficult to find a single copy of a high-affinity sequence among the billions of sequences that are accidentally carried forward through the partitioning step.

By contrast, acyclic identification allows the distinction of aptamers simply by counting the number of detected hits between different candidates and the target as indices of respective binding affinity, i.e., by ranking and mapping the level of affinity of multiple candidates. It has been described above how this approach easily located a known thrombin aptamer and lower-affinity variants, and a novel set of carbohydrate aptamers without resorting to time-consuming cyclic enrichment techniques that are the hallmarks of SELEX. However, as described above, the acyclic identification of aptamers (AIA) approach requires a library with multiple copies (in comparison to SELEX) of candidate aptamers in order to work. The cut-off for "R" (average copies of each distinct sequence) is about 3 and preferably about 200.

To raise the level of average representation or the R-value of an aptamer library so that acyclic method can be practiced to screen for high-affinity aptamers for a given target or targets, the present invention provides a method where a starting library (L1), often sparsely represented, is turned into an over-represented library (L3) through two steps. In the first step, sequence complexity in L1 is reduced, preferably by a factor of at least about 100, 1000, 10000 or even more to arrive at an intermediary library (L2). Then in a second step, L2 is amplified, e.g., through PCR, so that the average representation of each remaining aptamer candidate in the library is raised to the desired level, e.g., about 3, 200 or 1000.

Krylov and co-workers estimated, in Berezovski et al. *Nature Protocols* 1: 1359-1369 (2006), that the abundance of aptamers against a target exceeds $5 \times 10^{-10}$ (they utilized a very sparsely represented pool with m=39). Assuming that this estimate is reasonable, a pool containing 100 pmol of unique sequences should have at least $6 \times 10^{13} \times 5 \times 10^{-10} = 30,000$ aptamers for the target. This is a relatively large number and must include strong, medium and weakly binding sequences. Even if 30,000 aptamers is a generous estimate, $6 \times 10^{13}$ minus 30,000 is still $6 \times 10^{13}$ to the $9^{th}$ decimal place. Thus, it is likely that any individual target will consume only a tiny subset of all possible sequences, and there will be relatively few collisions except for similar substances. Thus, it is unlikely that individual targets in a pool of targets will cross-react extensively with the same aptamer, except for closely related targets, as for isoforms of the same protein or a protein with and without post-translational modifications.

Accordingly, in one aspect of the present invention, an over-represented library (an L3 library) is provided to screen for aptamers against a plurality of distinct targets simultaneously. In a preferred embodiment, the over-represented library has been previously conditioned to become biased towards yielding aptamer partners for these targets when the intermediary library (L2) has been partitioned against the same plurality of targets to reduce sequence complexity before amplification of the surviving sequences took place. Using this approach, it should also be possible to find aptamers that recognize common aspects of particular protein folds or epitopes for antibodies. For instance, combining L3 (or L4, L5, etc.) libraries generated from a sufficiently large plurality of proteins from animals, plants, fungi, protists, and prokaryotes should sample every available protein fold, every highly conserved protein domain, and a large variety of amino acid sequences that are typical epitopes for generating antibodies.

There are advantages in combining results from libraries of sparse representation and over-representation. For instance, ordinary SELEX that starts with a sparsely represented library can generate a template aptamer that can in turn be used as a guide in construction of over-represented libraries useful in acyclic identification methods. In an embodiment, an L1 starting library is constructed with primary structure and/or secondary structure found in the template aptamer. For instance, if the template aptamer has a stem-loop structure, the L1 library can be constructed with all the candidates having a stem-loop structure where the stem section keeps the sequence in the template while all or part of the loop section is varied to see if binding affinity can be modulated since the loop section is likely the region most responsible for interaction with the target.

Techniques inspired by SELEX that focus on highly efficient separations, see Berezovski M V et al. (2006); Nitsche A. et al. *BMC Bioiechnol* 7: 48 (2007); and Lou X et al. *Proc Natl Acad Sci USA* 106: 2989-2994 (2009), can also be coupled to high-throughput sequencing in either over-represented or sparsely-represented libraries. Further, over-represented and sparsely represented libraries can be mixed prior to partitioning. Acyclic identification is also compatible with many modified RNA nucleotides that are refractory to enzymatic replication of an evolving pool, but can be copied into DNA for sequencing, e.g., by reverse transcription. The latter is an aspect that can become crucial in applications of aptamers as therapeutics.

Acyclic identification should afford new opportunities for multiplexing targets. In the absence of cyclic evolution, aptamers with high affinity do not compete against those with moderate or low affinity. Thus, it is possible to mix multiple targets prior to partitioning against a library, and the aptamers matched to their individual targets in secondary screens. Multiplexing the targets was demonstrated in the co-isolation of aptamers for α-thrombin and carbohydrates described in detail in our WO2009/151688 patent publication.

The principal expense of AIA is the cost of high-throughput sequencing, which is more than offset by the reduction in the amount of target and labor needed to conduct multiple rounds or more of cyclic evolution. The sequencing cost can be reduced by multiplexing different identification experiments, as is routine for high-throughput sequencing platforms. As sequencers take leaps into billions and trillions of reads, acyclic identification will become even more attractive.

Example

Reduced Complexity Libraries Applied to Human Coagulation Factor IXa

Most possible sequences are absent from naïve (unpartitioned) SELEX pools, e.g., in 100 pmol of a pool with m=35 the probability is only $5 \times 10^{-8}$ that a particular 35 mer segment is present; virtually all of the $6 \times 10^{13}$ molecules in the pool occur as single copies. Despite this sparse representation, high affinity molecules come to dominate the evolving pool under the selective pressure of binding. Repeated motifs in the final pool identify aptamers.

Figure 2:
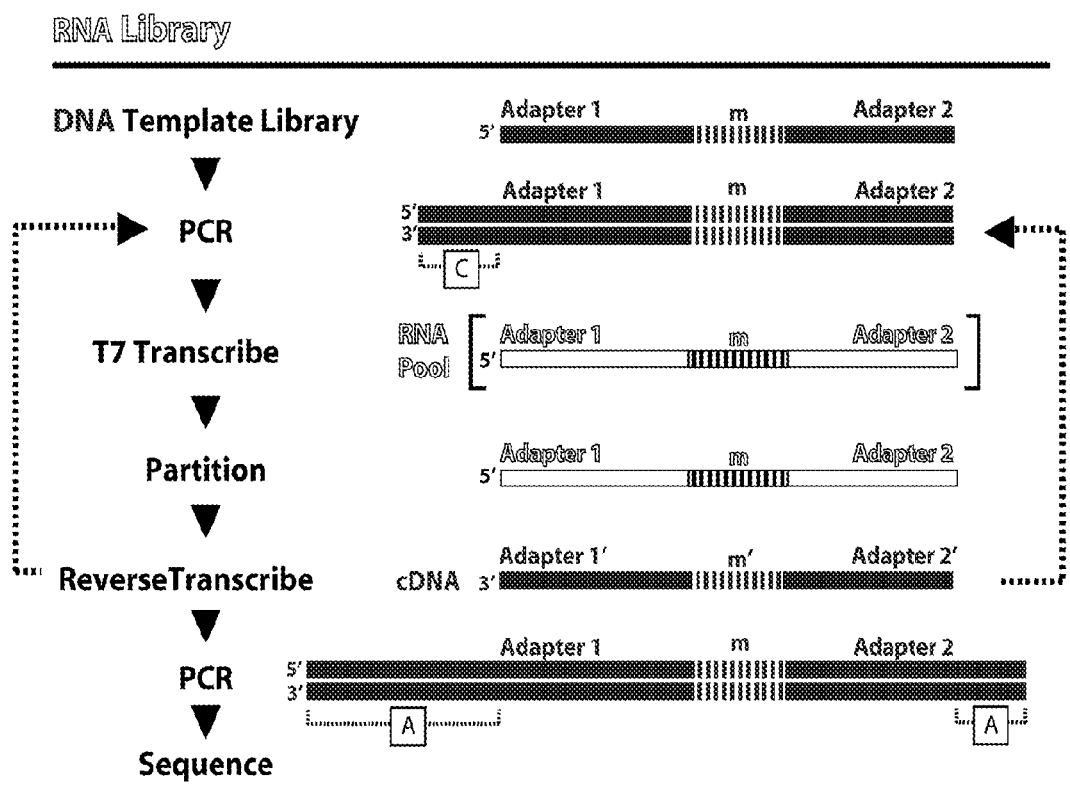
FIG. 2 shows the workflow for screening an m=35 RNA library. The strands are all DNA except for the steps labeled "T7 Transcribe" and "Partition" where they are RNA. The starting m=35 DNA library contains portions of modified Illumina sequencing adapters 1 & 2 flanking the randomized library region (m). PCR amplification is used to incorporate a T7 promoter at the 5' end (region C). An RNA pool is prepared via T7 transcription. The resulting L1 RNA library is partitioned against the target and then reverse transcribed into cDNA (L2). As described above, the resultant cDNA was PCR amplified using a primer that incorporates a T7 promoter, transcribed and purified to generate a reduced complexity, over-represented library, L3. This library was partitioned once more against the target and then prepared for Illumina GA sequencing via RT-PCR amplification (region A is required for clustering on Illumina flowcell), and sequenced on the Illumina GA IIx (read length of 43 nt).

According to the present invention, reduced-complexity, over-represented libraries are defined as having, on average, multiple copies of each molecule that is present, while a significant portion, even the majority of possible sequences, may be absent. Such a library can be prepared by partitioning a sparse pool against the target, followed by PCR amplification. Most sequences are removed by partitioning, and the survivors occur in multiple, e.g., hundreds to thousands of copies after PCR. AIA can then be used to distinguish and rank the aptamers. Note that all of the diversity in the parent library is applied to the target. The general scheme for reducing the complexity of RNA libraries is shown in FIG. 2.

AIA was used to discover an unprecedented family of aptamers in a reduced complexity, sparse library partitioned against human coagulation factor IXa (FIXa) (all RNA, m=35). 100 pmol of the naïve RNA pool (L1) was partitioned against FIXa to eliminate most of the nonbinding molecules. Reverse transcription, PCR, and transcription by T7 RNA polymerase were used to prepare an over-represented offspring pool (L3), which is estimated to have 1,000 to 10,000 copies of each survivor. AIA on 100 pmol of this offspring pool L3 yielded 46 unique sequences counted ≥50 times, and 16 new aptamer families having closely related variants.

Figure 3:
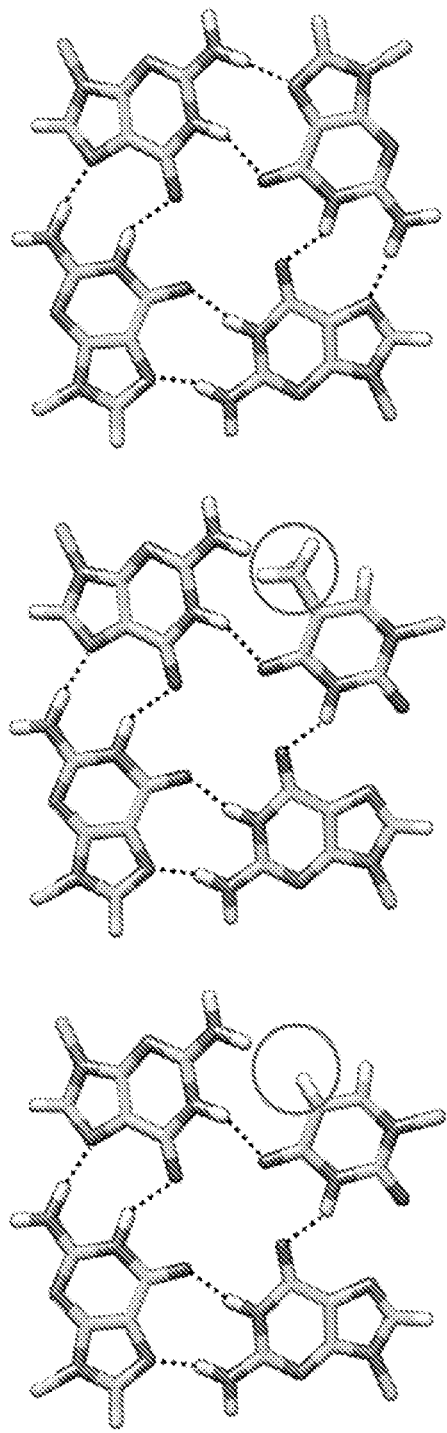
FIG. 3 depicts the difference between base planes in quadruplexes, (top) G4, (middle) $G_3T$ and (bottom) $G_3U$. The circled groups show steric interference of the T-methyl with the neighboring G-amino (middle), and the relief of this interference when U replaces T.

The novel FIXa aptamer candidates are all consistent with an aptamer motif: Q1-L1-Q2-L2-Q3-L3-Q4-Tail (see Table 3 below). The nine most abundant sequences were all counted ≥1,000 times. Regions, Q, are rich in G and U (96% G+U, G:U=2.3:1), and probably form quadruplex segments where U occasionally substitutes for G. Such substitutions in RNA base-quadruples should be more favourable than in DNA where there is steric interference of the 5-methyl of T and the G-2-amino of its Hoogsteen partner (FIG. 3). Substituting U for G may create new quadruplex shapes for target recognition. The L-segments are putative loops, rich in C and A; these bases have similar functional groups and often replace each other in variants of the top nine aptamers. The Q-regions may involve two or three sets of base quadruples, including UGG from the 5'-flanking region. Analysis using ClustalX showed that each of the nine most abundant sequences had two to nine variant sequences, where G to U or U to G substitutions were common in putative Q-regions, and A to C or C to A in putative L-regions; these are substitutions that are most conservative with respect to H-bonding capabilities. Affinities of FIXa for the three highest ranked aptamers are in the range of Kd=200-700 nM (Table 3). Functional assays showed 50% inhibition of 0.1 nM FIXa at ~20 μM of aptamers with high counts.

Earlier it was mentioned that AIA affords new opportunities for multiplexing samples. Aptamers with high affinity do not eliminate those with moderate affinity in AIA as there is no evolution. Thus, multiple targets can be mixed prior to partitioning against a library, and the aptamers matched to their individual targets in secondary screens. Multiplexing the targets has been demonstrated in the co-isolation of aptamers for α-thrombin and carbohydrates, see WO2009/151688 patent publication. Now it should be clear that, fully represented and reduced complexity libraries can be mixed. The cost of massively parallel sequencing for AIA can also be reduced by multiplexing identification experiments, as is sometimes used for second-generation sequencers. Widespread application of AIA should help aptamers fulfill their promise as replacements for antibodies in many applications.

The overall result of this example demonstrated the successful generation of an over-represented RNA library (L3) where the sequence complexity was reduced by one round of partitioning against the target FIXa. It is also shown that L3 is suitable for aptamer identification using our AIA procedure. Modifications to apply the scheme in FIG. 2 to sparsely represented DNA libraries (to prepare over-represented reduced complexity libraries) will be obvious to those skilled in the art of molecular biology and high throughput sequencing and are contemplated to be part of the invention. It is also contemplated that similar schemes can be used to reduce the complexity of fully represented RNA, DNA, or modified DNA/RNA libraries. Finally, the scheme can be adapted to the use of multiple targets for reducing the complexity of the starting L1 library.

TABLE 3

Properties of High Ranking Aptamers[a] for Factor IXa with m = 35

| SEQ ID NO: | Rank | Sequence | Count | $K_d$ (nM)[b] |
|---|---|---|---|---|
| | | Q1-----L1---------Q2-------L2 <br> Q3-----L3---------Q4-------Tail-aaG | | |
| 150 | 1 | UGGUU--ccaGUc-----GGUG-----aacUUcc- <br> UGaGU--cc---------GGUGUGUG-c- | 7,192 | ~220 |
| 151 | 2 | UGG----a----------GGG------caGccc- <br> GGU----aGUcGcccac-GGGG-----aacGcGUc- | 6,311 | ~220 |
| 152 | 3 | UGG----caUacGcGca-GG-------cUGGa- <br> GGU----aUUacccc--GGG------c- | 5,562 | ~700 |

[a]G and T/U are shown in capitals, a and c in lowercase font.
[b]Affinities estimated by electrophoretic mobility shift compared to a known aptamer for Factor IXa.
[c]Sequence of the variable region is shown in regular font. Underlined bases denote substitutions observed in variants of each parent sequence. Conservative substitutions of functional groups, G/T and c/a, are marked in single underline, other substitutions in double underline. Dashes separate putative quadruplex and loop regions. Italics denote fixed regions. Flanking sequences are given in Methods.

TABLE 4

ClustalX sequence alignment of the top 46 aptamers for human coagulation factor IXa (counts ≥50). Rank and count are indicated at left, with the top 9 highlighted. Underlining denotes substitutions observed in variants of a family, compared to the parent.

| SEQ ID NO: | Rank_Count | Sequence in Randomized Region[a] |
|---|---|---|
| 104 | 8_1427 | -------GaaGGaaUGUccGUccccaccUGcGGUUGGcUUGa------ |
| 105 | 35_73 | --------GaaGGaaUGUccGUccccaccUGcGGGUGGcUUGa------ |
| 106 | 45_51 | --------GaaGGaaUGUccGUccccaccUGcGGUUGGGUUGa------ |
| 107 | 37_70 | --------GaaGGaaUGUccGUccccaccUGcGGUUGGcUUGc------ |
| 108 | 38_67 | --------GaaGGaaUGUccGUccccaccUGcGGUUGGcUUGG------ |
| 109 | 27_118 | -------GaaGGaaUGUccGUccccaccUGcGGUUGGcUUUa------ |
| 110 | 5_2701 | ----------acGaUUGUccccca-GaGUGUUGcacGcacGUccGG-- |
| 111 | 41_62 | -----------acGaUUGUccccca-GaGUGUUGcacGcccGUccGG-- |
| 112 | 20_215 | ---------UGcaGUUGcUaGaaGcaaGUGUGGcaGccGcGGGG---- |
| 113 | 33_80 | ---------UGcaGUUGcUaGaaGcaaGUGUGGcaGGcGcGGGG---- |
| 114 | 2_6311 | -------------aGGGcaGcccGGUaGUcGcccacGGGGaacGcGUc |
| 115 | 18_217 | -------------aGGGcaGcccGGUaGUcGcccacGGGGcacGcGUc |
| 116 | 30_92 | -------------aGGGcaGcccGGUaGUcGcccacGGGGaccGcGUc |
| 117 | 19_216 | -------------aGGGcaGcccGGUaGUcGcccacGGGGaaaGcGUc |
| 118 | 29_93 | -------------aGGGcaGcccGGUaGUcGcccacGGGGaacGGGUc |
| 119 | 15_327 | -------------aGGGcaGcccGGUaGUcGccccGGGGaacGcGUc |
| 120 | 34_77 | -------------aGGGcaGcccGGUaGUcGcccccGGGGaacGcGGc |
| 121 | 11_688 | -------------aGGGcaGcccGGUaGUcGcccacGGGGaacGcGGc |

TABLE 4-continued

ClustalX sequence alignment of the top 46 aptamers for human coagulation factor IXa (counts ≥50). Rank and count are indicated at left, with the top 9 highlighted. Underlining denotes substitutions observed in variants of a family, compared to the parent.

| 122 | 3_5562  | --------UcaUacGcGcaGGcUGGaGGUaUUaccccccGGGc----- |
| --- | ------- | ------------------------------------------------ |
| 123 | 28_113  | --------UcaUacGcGcaGGcUGGaGGUaUUaaccccccGGGc----- |
| 124 | 42_58   | ---------UcaUacGcGcaGGcUGGaGGUaUUcccccccGGGc----- |
| 125 | 10_705  | --------UcaUacGcGcaGGcUGGaGGGaUUaccccccGGGc----- |
| 126 | 43_57   | ---------UcaUacGcGcaGGcUGGaGGGaUUaccccccGGGG----- |
| 127 | 16_278  | --------UcaUacGcGcaGGcUGGaGGUaUUaccccccGGGG----- |
| 128 | 14_402  | -------UccGGGaacGcGGcGcGcUaaaGGUGGaccUcGca------ |
| 129 | 12_641  | ----------aUaGcUcGGcaUGaGaGGGccaGcUacGcaUGccG--- |
| 130 | 40_65   | ----------aUaGcUcGGcaUGaGaGGGccaGcUaaGcaUGccG--- |
| 131 | 36_71   | ----------aUaGcUcGGcaUGaGaGGGccaGcUacGccUGccG--- |
| 132 | 13_635  | ------------GGUcGcaaacGaaaUGccUaacUaGacaUGcaGcc- |
| 133 | 1_7192  | -----UUccaGUcGGUGaacUUccUGaGUccGGUGUGUGc-------- |
| 134 | 22_179  | -----UUccaGUcGGUGaacUUccUGaGUccGGGGUGUGc-------- |
| 135 | 26_133  | -----UUccaGUcGGUGaacUUccUGaGUccGGUGUGGGc-------- |
| 136 | 46_50   | ------UUccaGUcGGUGcacUUccUGaGUccGGUGUGGGc-------- |
| 137 | 32_84   | ------UUccaGUcGGUGaacUUccUGaGUccGGUGGGUGc-------- |
| 138 | 4_3251  | -----------UccaaGcaUaaccUGUGUccGGUaGaUcaUGcccG   |
| 139 | 17_256  | UcacacGGUacGUGcaaGcaU--ccUacGUUUGGUca------------ |
| 140 | 6_2456  | -------UcGccGGGUacccaUUccaGGGGGGGaUcGGUcGU------ |
| 141 | 31_86   | --------UcGccGGGUacccaUUccaGGGGGGGaUcGGUcGG------ |
| 142 | 44_57   | --------UcGccGGGUacccaUUccaGGGGGGGcUcGGUcGU------ |
| 143 | 9_1414  | ------acaGGaUGGUUUcGcUUUUaGaUGcGGUaaGUGca------- |
| 144 | 23_174  | ------acaGGaUGGUUUcGcUUUUaGaUGcGGGaaGUGca------- |
| 145 | 24_148  | ------acaGGaUGGUUUcGcUUUUaGaUGcGGUaaGGGca------- |
| 146 | 21_180  | ------acaGGaUGGUUUcGcUUUUaGaUGcGGUaaGUGcc------- |
| 147 | 25_143  | ----------aaGGcGUUaacGGGaUGcGUcUcacGGUcaUcGGc- |
| 148 | 39_65   | -------acaGGGUGacacccUccacUcGUccUcaaUGUGcc------- |
| 149 | 7_2409  | -----------GaaUGUacUUGGUUGcUccUUGccccGcGUaGUc- |

Note for Table 4:
*Each 35-nucleotide sequence listed above had a 5'-flanking sequence (F5): 5'-ACGACGCTCTTCCGATCTATGG, (SEQ ID NO: 153) and a 3'-flanking sequence (F3): 5'-AAGCTAACGGAGCTCGTATGC (SEQ ID NO: 154).

coagulation factor IXa (counts ≥50). Rank and count are indicated at left, with the top 9 highlighted. Underlining denotes substitutions observed in variants of a family, compared to the parent.

Note for Table 4:
"Each 35-nucleotide sequence listed above had a 5'-flanking sequence (F5):
5'-ACGACGCTCTTCCGATCTATGG, (SEQ ID NO:153) and a 3'-flanking sequence (F3): 5'-AAGCTAACGGAGCTCGTATGC (SEQ ID NO:154).

Methods
Reduced Complexity RNA Library.
A starting m=35 DNA library was purchased from IDT (Coralville, Iowa) from which 100 pmol was PCR amplified to incorporate a T7 promoter at the 5'-end. PCR conditions were: (a) 2 min at 94° C., (b) 35 cycles of (1 min at 94° C., 1 min at 52° C., and 1 min at 72° C.), (c) 10 min at 72° C. The amplified library was purified using a QIAquick PCR purification kit (QIAGEN) and 100 pmol was transcribed into RNA using an AmpliScribe T7 high yield transcription kit (Epicentre Technologies). The transcribed RNA library was purified on a G-25 gel filtration column (GE) after phenol extraction and ethanol precipitation. 100 pmol of the purified RNA library was partitioned once against FIXa as described below. The partitioned RNA library was reverse transcribed into cDNA with a sequence-specific primer using a Thermoscript RT-PCR kit (Invitrogen). The RT reaction conditions were:

60 min at 50° C. followed by 5 min at 85° C. As described above, the resultant cDNA was PCR amplified, transcribed and purified again to generate an over-represented reduced complexity RNA library (m=35) that was used to identify aptamers.

Aptamer Partitioning.

The partitioning step followed Bock et al. (1992) as detailed in WO2009/151688 patent publication. Target library (100 pmol) in 1 mL of partitioning buffer (20 mM Tris-HCl, 140 mM NaCl, 5 mM KCl, 1 mM $CaCl_2$ and 1 mM $MgCl_2$ at pH 7.4) was negatively partitioned in a 1 mL slurry of con-A beads (Pierce) pre-equilibrated in partitioning buffer at 25° C., and then applied to 6 nmol of FIXa (Haematologic Technologies) immobilized on 1 mL of pre-equilibrated con-A beads. After washing with buffer, nucleic acid-protein complexes were eluted with 0.1 M α-methyl-mannoside, and the DNA/RNA was recovered by phenol extraction and ethanol precipitation as described in Sambrook 1, et al. (2001) Molecular Coning: A Laboratory Manual: Cold Spring Harbor Press.

Preparation for HT Sequencing.

Library for m=35.

The reduced complexity RNA library after partitioning was reverse transcribed into cDNA with a sequence-specific primer. The RT reaction conditions were: 60 min at 50° C. followed by 5 min at 85° C. The cDNA was PCR amplified to extend the flanking regions for clustering on Illumina flow-cell. PCR conditions were: (a) 2 min at 94° C., (b) 6 cycles of (1 min at 94° C., 1 min at 52° C., and 1 min at 72° C.), (c) 24 cycles of (1 min at 94° C., 1 min at 61° C., and 1 min at 72° C.), (d) 10 min at 72° C. The PCR product was purified using the QIAquick PCR purification kit and size checked on a 4% agarose gel.

Sequence Analysis.

A PERL script was used to identify sequence strings that closely matched the F5-m-F3 region (see [1] for details of the script and definitions for the match regions within F5 and F3, which are adjacent to the central region of m bases. The match criteria were used to generate a file of Qualified reads for sequences with the desired length of central m-bases, and multiples of any unique sequences were counted and ranked from highest count to lowest.

Table 4 gives overall statistics on the sequences. Most sequences that are counted one time only arise from molecules that have little affinity for the target and are accidentally carried forward in the partitioning step. The read length for m=35 was seven bases more than for thrombin. This may contribute to an increase in the percent of bad reads for this experiment.

TABLE 4

Sequencing Statistics for Acyclic Identification of Aptamers for Factor IXa from a Reduced Complexity Library with m = 35.

| | |
|---|---|
| Length of read | 43 |
| Total reads | 9,196,135 |
| Total qualified reads | 4,424,584 |
| Percent qualified reads | 48% |
| Total unique sequences | 1,277,353 |
| Number of unique sequences counted 1 time only | 694,135 |
| Percent of qualified reads counted one time only | 16% |
| No. unique sequences counted twice | 85.556 |
| No. unique sequences counted 3 times | 66,412 |
| No. unique sequences counted between 4-10 times | 357,195 |
| No. unique sequences counted between 11-25 times | 73,457 |
| No. unique sequences counted between 26-50 times | 553 |
| No. unique sequences counted between 51-100 times | 17 |
| No. unique sequences counted between 101-250 times | 11 |
| No. unique sequences counted between 251-500 times | 4 |
| No. unique sequences counted > 500 times | 13 |

Electrophoretic Mobility Shift Assay

Aptamer candidates were pre-incubated for 30 minutes with other components as explained in each corresponding legend. Samples were analyzed on native polyacrylamide gels (14% (w/v)) in 1×Tris/glycine running buffer at 100V for 45 min at 4° C. Immediately after electrophoresis, gels were stained with SYBR gold for 1 hour, imaged and stained with Coomassie Brilliant Blue.

Functional Assays.

Enzymatic activity of FIXa was measured using a BIOPHEN FIXa kit (Aniara, Ohio) at 0.1 nM FIXa and 20 μM aptamers (where present) final concentrations. Briefly, FIXa samples with and without aptamers were pre-incubated for 20 min at 4° C. Human Factor X and Factor VIII:C were added and incubated for 2 min at 37° C. Then human thrombin, calcium and synthetic phosphlipids were added and incubated for 3 min at 37° C. The activity of FIXa was measured by its activation of Factor X using a Factor Xa chromogenic synthetic peptide substrate that released para-nitroanaline; the latter was quantified by determining its absorbance at 405 nm.

DNA/RNA Sequences.

All sequences are listed in 5' to 3' direction, m=degenerate bases (library region). Note: Splints 1 & 2 (Supplementary FIG. S2) possess overhangs complementary to the constant stem and tail regions of the library from each direction. The forward PCR primer also introduced a 5' overhang complementary to an oligomer planted on the Illumina flowcell, to anneal the amplified library for sequencing.

FACTOR IXa Experiments for m=35 m=35 DNA library

ACGACGCTCTTCCGATCTATGG-$m^{35}$-AAGCTAACGGAGCTCGTATGC (SEQ ID NO:155)

T7 PCR forward primer

TAATACGACTCACTATAGGAC-GACGCTCTTCCGATCT (SEQ ID NO:156)

T7 PCR reverse primer/Reverse Transcription Primer

GCATACGAGCTCCGTTAGCTT (SEQ ID NO:157)

PCR forward primer

AATGATACGGCGACCACCGAGATCTA-CACTCTTTCCCTGGACGACGCTCT TCCGATCT (SEQ ID NO:158)

PCR reverse primer

CAAGCAGAAGACGGCATACGAGCTCCGTTAGCTT (SEQ ID NO:159)

Sequencing Primer

ACACTCTTTCCCTGGACGACGCTCTTCCGATCT (SEQ ID NO:160)

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the presently disclosure material.

Sequence listings and related materials in the ASCII text file named "2011-05-18_APX-001PCT_Seq_Listing_ST25.txt" and created on May 18, 2011 with a size of about 33 kilobytes, is hereby incorporated by reference.

The invention claimed is:

1. A method for identifying an aptamer that binds to a target comprising the steps of:
   (a) providing a plurality of starting libraries each comprising a starting pool of aptamer candidates, each of said aptamer candidates of substantially the same length while having a primary structure and at least one common pre-selected secondary structure, said primary structure comprising at least a variable nucleotide sequence where nucleotides at "m" number of positions are being varied, said common pre-selected secondary structure varying among said plurality of starting libraries;
   (b) reducing the sequence complexity in each of said plurality of starting starting libraries by a factor of at least about 100 to a plurality of intermediary libraries of surviving aptamer candidates;
   (c) amplifying each of said plurality of intermediary libraries to a plurality of over-represented libraries of said surviving aptamer candidates such that, for every 100 pmol of said surviving aptamer candidates, each surviving aptamer candidate has, on average, at least about three copies;
   (d) mixing said plurality of over-represented libraries into a comprehensive library with surviving aptamer candidates of varying secondary structures;
   (e) contacting said comprehensive library with a target under a buffer condition that allows binding between members of said comprehensive library and said target;
   (f) isolating at least one aptamer candidate that is bound to said target; and
   (g) determining the sequence of said bound aptamer candidate.

2. The method of claim 1 wherein said starting library is sparsely represented.

3. The method of claim 1, wherein said pre-selected secondary structure is selected from the group consisting of a hairpin loop, a bulge loop, an internal loop, a multi-branch loop, and a pseudoknot.

4. The method of claim 1, wherein in step (d), at least about 10 over-represented libraries are mixed into a comprehensive library.

5. The method of claim 1 wherein at least one of said plurality of starting libraries is contacted with parts or substantially the entire content of a cellular lysate.

6. The method of claim 1, wherein each of said starting libraries comprises at least $10^9$ distinct aptamer candidates.

7. The method of claim 1, wherein said step (f) further comprises ranking target-binding affinity of a plurality of bound aptamer candidates.

* * * * *

SEQUENCE LISTING

<160> NUMBER OF SEQ ID NOS: 160

<210> SEQ ID NO 1
<211> LENGTH: 39
<212> TYPE: DNA
<213> ORGANISM: Artificial sequence
<220> FEATURE:
<223> OTHER INFORMATION: Nucleotide aptamer sequence
<220> FEATURE:
<221> NAME/KEY: variation
<222> LOCATION: (13)..(27)
<223> OTHER INFORMATION: Any or all of nucleotide "n" at 13-27 can
      either be absent or present.
<220> FEATURE:
<221> NAME/KEY: misc_feature
<222> LOCATION: (13)..(27)
<223> OTHER INFORMATION: "n" is any nucleotide.

<400> SEQUENCE: 1
acacgcgcat gcnnnnnnnn nnnnnnngca tgcgccaca                              39

<210> SEQ ID NO 2
<211> LENGTH: 12
<212> TYPE: DNA
<213> ORGANISM: Artificial sequence
<220> FEATURE:
<223> OTHER INFORMATION: Flanking sequence to aptamer candidates

<400> SEQUENCE: 2
acacgcgcat gc                                                          12

<210> SEQ ID NO 3
<211> LENGTH: 12
<212> TYPE: DNA
<213> ORGANISM: Artificial sequence
<220> FEATURE:
<223> OTHER INFORMATION: Flanking sequence to aptamer candidates

<400> SEQUENCE: 3
gcatgcgcca ca                                                          12

<210> SEQ ID NO 4
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 4
ggttggtgtg gttgg                                                       15

<210> SEQ ID NO 5
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 5
ggttggtgtg gtttg                                                       15

<210> SEQ ID NO 6
<211> LENGTH: 15
<212> TYPE: DNA
<213> ORGANISM: Artificial sequence
<220> FEATURE:
<223> OTHER INFORMATION: Nucleotide aptamer sequence

```
<400> SEQUENCE: 6
ggttggtgtt gttgg                                                    15

<210> SEQ ID NO 7
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 7
ggttggtgtg gttgt                                                    15

<210> SEQ ID NO 8
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 8
ggttggtttg gttgg                                                    15

<210> SEQ ID NO 9
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 9
ggctggtgtg gttgg                                                    15

<210> SEQ ID NO 10
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 10
ggttggtgtg tttgg                                                    15

<210> SEQ ID NO 11
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 11
ggttggcgtg gttgg                                                    15

<210> SEQ ID NO 12
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 12
ggttggtgtt gtttg                                                    15

<210> SEQ ID NO 13
<211> LENGTH: 15
```

```
<212> TYPE: DNA
<213> ORGANISM: Artificial sequence
<220> FEATURE:
<223> OTHER INFORMATION: Nucleotide aptamer sequence

<400> SEQUENCE: 13
ggttggtgtg gctgg                                                     15

<210> SEQ ID NO 14
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 14
ggtttgtgtg gttgg                                                     15

<210> SEQ ID NO 15
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 15
ggttggtgtg gtttt                                                     15

<210> SEQ ID NO 16
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 16
ggttgttgtg gttgg                                                     15

<210> SEQ ID NO 17
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 17
ggttggggtg gttgg                                                     15

<210> SEQ ID NO 18
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 18
ggttggtgcg gttgg                                                     15

<210> SEQ ID NO 19
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 19
```
ggttggtgtg gtcgg                                                         15

<210> SEQ ID NO 20
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 20
ggtcggtgtg gttgg                                                         15

<210> SEQ ID NO 21
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 21
gggtggtgtg gttgg                                                         15

<210> SEQ ID NO 22
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 22
ggttggtgtg gttgc                                                         15

<210> SEQ ID NO 23
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 23
ggttggtttg gtttg                                                         15

<210> SEQ ID NO 24
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 24
ggttggtctg gttgg                                                         15

<210> SEQ ID NO 25
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 25
ggttggtgtg ggtgg                                                         15

<210> SEQ ID NO 26
<211> LENGTH: 15
<212> TYPE: DNA
<213> ORGANISM: Artificial sequence

```
<220> FEATURE:
<223> OTHER INFORMATION: Nucleotide aptamer sequence

<400> SEQUENCE: 26
ggttggtgtc gttgg                                                    15

<210> SEQ ID NO 27
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 27
ggttcgtgtg gttgg                                                    15

<210> SEQ ID NO 28
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 28
ggttggtgtg gttcg                                                    15

<210> SEQ ID NO 29
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 29
cgttggtgtg gttgg                                                    15

<210> SEQ ID NO 30
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 30
ggttgctgtg gttgg                                                    15

<210> SEQ ID NO 31
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 31
gcttggtgtg gttgg                                                    15

<210> SEQ ID NO 32
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 32
ggttggtgtt gttgt                                                    15
```

```
<210> SEQ ID NO 33
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 33
ggttggtgtg cttgg                                                         15

<210> SEQ ID NO 34
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 34
agttggtgtg gttgg                                                         15

<210> SEQ ID NO 35
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 35
ggttggtgtg ttttg                                                         15

<210> SEQ ID NO 36
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 36
ggttggtggg gttgg                                                         15

<210> SEQ ID NO 37
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 37
ggttggagtg gttgg                                                         15

<210> SEQ ID NO 38
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 38
ggttggtatg gttgg                                                         15

<210> SEQ ID NO 39
<211> LENGTH: 15
<212> TYPE: DNA
<213> ORGANISM: Artificial sequence
<220> FEATURE:
<223> OTHER INFORMATION: Nucleotide aptamer sequence
```

```
<400> SEQUENCE: 39
ggttggtgtt gtttt                                                          15

<210> SEQ ID NO 40
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 40
ggttggtttt gttgg                                                          15

<210> SEQ ID NO 41
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 41
ggtgggtgtg gttgg                                                          15

<210> SEQ ID NO 42
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 42
tgttggtgtg gttgg                                                          15

<210> SEQ ID NO 43
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 43
ggttggtgta gttgg                                                          15

<210> SEQ ID NO 44
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 44
ggatggtgtg gttgg                                                          15

<210> SEQ ID NO 45
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 45
ggttagtgtg gttgg                                                          15

<210> SEQ ID NO 46
```

```
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 46
ggttggtgtg gttag                                                    15

<210> SEQ ID NO 47
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 47
ggttggtgag gttgg                                                    15

<210> SEQ ID NO 48
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 48
ggttggtgtg attgg                                                    15

<210> SEQ ID NO 49
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 49
ggttggtgtg tttgt                                                    15

<210> SEQ ID NO 50
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 50
ggttggtgtg gatgg                                                    15

<210> SEQ ID NO 51
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 51
ggtttgtgtg gtttg                                                    15

<210> SEQ ID NO 52
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 52
```
gattggtgtg gttgg            15

<210> SEQ ID NO 53
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 53
ggttggtgtg gttga            15

<210> SEQ ID NO 54
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 54
gctatcatcg caacg            15

<210> SEQ ID NO 55
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 55
gctatcatcg ccacg            15

<210> SEQ ID NO 56
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 56
gctatcatcg caccg            15

<210> SEQ ID NO 57
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 57
gctctcatcg caacg            15

<210> SEQ ID NO 58
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 58
gctatcatcg caacc            15

<210> SEQ ID NO 59
<211> LENGTH: 15
<212> TYPE: DNA

```
<213> ORGANISM: Artificial sequence
<220> FEATURE:
<223> OTHER INFORMATION: Nucleotide aptamer sequence

<400> SEQUENCE: 59
gctatcctcg caacg                                                        15

<210> SEQ ID NO 60
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 60
gctatcatcg caaag                                                        15

<210> SEQ ID NO 61
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 61
gctatcatcc caacg                                                        15

<210> SEQ ID NO 62
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 62
gctattatcg caacg                                                        15

<210> SEQ ID NO 63
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 63
gctctcatcg ccacg                                                        15

<210> SEQ ID NO 64
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 64
gctatcatcg caatg                                                        15

<210> SEQ ID NO 65
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 65
gctatcatct caacg                                                        15
```

<210> SEQ ID NO 66
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 66
gctaccatcg caacg                                                    15

<210> SEQ ID NO 67
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 67
gccatcatcg caacg                                                    15

<210> SEQ ID NO 68
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 68
gctatcatcg ctacg                                                    15

<210> SEQ ID NO 69
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 69
gctttcatcg caacg                                                    15

<210> SEQ ID NO 70
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 70
gctatcattg caacg                                                    15

<210> SEQ ID NO 71
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 71
gctatcatcg caact                                                    15

<210> SEQ ID NO 72
<211> LENGTH: 15
<212> TYPE: DNA
<213> ORGANISM: Artificial sequence
<220> FEATURE:

<223> OTHER INFORMATION: Nucleotide aptamer sequence

<400> SEQUENCE: 72
gctatcaccg caacg                                                     15

<210> SEQ ID NO 73
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 73
gctatcatcg ccccg                                                     15

<210> SEQ ID NO 74
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 74
gctatcatcg catcg                                                     15

<210> SEQ ID NO 75
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 75
gctatcatag caacg                                                     15

<210> SEQ ID NO 76
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 76
gatatcatcg caacg                                                     15

<210> SEQ ID NO 77
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 77
gctctcatcg caccg                                                     15

<210> SEQ ID NO 78
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 78
gctatcatcg aaacg                                                     15

```
<210> SEQ ID NO 79
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 79
gctatcatcg gaacg                                                  15

<210> SEQ ID NO 80
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 80
gctatcctcg caccg                                                  15

<210> SEQ ID NO 81
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 81
gctatcttcg caacg                                                  15

<210> SEQ ID NO 82
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 82
gctatcatcg taacg                                                  15

<210> SEQ ID NO 83
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 83
actatcatcg caacg                                                  15

<210> SEQ ID NO 84
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 84
gctataatcg caacg                                                  15

<210> SEQ ID NO 85
<211> LENGTH: 15
<212> TYPE: DNA
<213> ORGANISM: Artificial sequence
<220> FEATURE:
<223> OTHER INFORMATION: Nucleotide aptamer sequence
```

<400> SEQUENCE: 85
cctatcatcg caacg                                                      15

<210> SEQ ID NO 86
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 86
gctatcatcc caacc                                                      15

<210> SEQ ID NO 87
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 87
gctatcatca caacg                                                      15

<210> SEQ ID NO 88
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 88
gctatcatcg caagg                                                      15

<210> SEQ ID NO 89
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 89
gctatcatcg caaca                                                      15

<210> SEQ ID NO 90
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 90
gttatcatcg caacg                                                      15

<210> SEQ ID NO 91
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 91
gctatcatcg cacag                                                      15

<210> SEQ ID NO 92
<211> LENGTH: 15

-continued

<212> TYPE: DNA
<213> ORGANISM: Artificial sequence
<220> FEATURE:
<223> OTHER INFORMATION: Nucleotide aptamer sequence

<400> SEQUENCE: 92
gctgtcatcg caacg                                                    15

<210> SEQ ID NO 93
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 93
gctatcatcg caaac                                                    15

<210> SEQ ID NO 94
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 94
gctctcatcg ccccg                                                    15

<210> SEQ ID NO 95
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 95
gctatcatcg ccacc                                                    15

<210> SEQ ID NO 96
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 96
gctatcatcg cgacg                                                    15

<210> SEQ ID NO 97
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 97
ggtatcatcg caacg                                                    15

<210> SEQ ID NO 98
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 98
gctagcatcg caacg                                                          15

<210> SEQ ID NO 99
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 99
tctatcatcg caacg                                                          15

<210> SEQ ID NO 100
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 100
gctatcatcc ccacg                                                          15

<210> SEQ ID NO 101
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 101
gcgatcatcg caacg                                                          15

<210> SEQ ID NO 102
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 102
gctatcatcg caccc                                                          15

<210> SEQ ID NO 103
<211> LENGTH: 15
<212> TYPE: DNA
<213> ORGANISM: Artificial sequence
<220> FEATURE:
<223> OTHER INFORMATION: Nucleotide aptamer sequence

<400> SEQUENCE: 103
gctatcatcg acacg                                                          15

<210> SEQ ID NO 104
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 104
gaaggaaugu ccgucccac cugcgguugg cuuga                                     35

<210> SEQ ID NO 105
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 105
gaaggaaugu ccgucccac cugcgggugg cuuga                    35

<210> SEQ ID NO 106
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 106
gaaggaaugu ccgucccac cugcgguugg guuga                    35

<210> SEQ ID NO 107
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 107
gaaggaaugu ccgucccac cugcgguugg cuugc                    35

<210> SEQ ID NO 108
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 108
gaaggaaugu ccgucccac cugcgguugg cuugg                    35

<210> SEQ ID NO 109
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 109
gaaggaaugu ccgucccac cugcgguugg cuuua                    35

<210> SEQ ID NO 110
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 110
acgauugucc cccagagugu ugcacgcacg uccgg                    35

<210> SEQ ID NO 111
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 111
acgauugucc cccagagugu ugcacgcccg uccgg                    35

<210> SEQ ID NO 112
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 112
ugcaguugcu agaagcaagu guggcagccg cgggg     35

<210> SEQ ID NO 113
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 113
ugcaguugcu agaagcaagu guggcaggcg cgggg     35

<210> SEQ ID NO 114
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 114
agggcagccc gguagucgcc cacggggaac gcguc     35

<210> SEQ ID NO 115
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 115
agggcagccc gguagucgcc cacggggcac gcguc     35

<210> SEQ ID NO 116
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 116
agggcagccc gguagucgcc cacggggacc gcguc     35

<210> SEQ ID NO 117
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 117
agggcagccc gguagucgcc cacggggaaa gcguc     35

<210> SEQ ID NO 118
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 118
agggcagccc gguagucgcc cacggggaac ggguc       35

<210> SEQ ID NO 119
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 119
agggcagccc gguagucgcc cccggggaac gcguc       35

<210> SEQ ID NO 120
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 120
agggcagccc gguagucgcc cccggggaac gcggc       35

<210> SEQ ID NO 121
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 121
agggcagccc gguagucgcc cacggggaac gcggc       35

<210> SEQ ID NO 122
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 122
ucauacgcgc aggcuggagg uauuaccccc cgggc       35

<210> SEQ ID NO 123
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 123
ucauacgcgc aggcuggagg uauuaacccc cgggc       35

<210> SEQ ID NO 124
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 124
ucauacgcgc aggcuggagg uauucccccc cgggc       35

<210> SEQ ID NO 125

-continued

```
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 125
ucauacgcgc aggcuggagg gauuacccccc cgggc                         35

<210> SEQ ID NO 126
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 126
ucauacgcgc aggcuggagg gauuacccccc cgggg                         35

<210> SEQ ID NO 127
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 127
ucauacgcgc aggcuggagg uauuacccccc cgggg                         35

<210> SEQ ID NO 128
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 128
uccgggaacg cggcgcgcua aagguggacc ucgca                          35

<210> SEQ ID NO 129
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 129
auagcucggc augagagggc cagcuacgca ugccg                          35

<210> SEQ ID NO 130
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 130
auagcucggc augagagggc cagcuaagca ugccg                          35

<210> SEQ ID NO 131
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 131
```
auagcucggc augagagggc cagcuacgcc ugccg                                      35

<210> SEQ ID NO 132
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 132
ggucgcaaac gaaaugccua acuagacaug cagcc                                      35

<210> SEQ ID NO 133
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 133
uuccagucgg ugaacuuccu gaguccggug ugugc                                      35

<210> SEQ ID NO 134
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 134
uuccagucgg ugaacuuccu gaguccgggg ugugc                                      35

<210> SEQ ID NO 135
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 135
uuccagucgg ugaacuuccu gaguccggug ugggc                                      35

<210> SEQ ID NO 136
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 136
uuccagucgg ugcacuuccu gaguccggug ugugc                                      35

<210> SEQ ID NO 137
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 137
uuccagucgg ugaacuuccu gaguccggug ggugc                                      35

<210> SEQ ID NO 138
<211> LENGTH: 35
<212> TYPE: RNA

```
<213> ORGANISM: Artificial sequence
<220> FEATURE:
<223> OTHER INFORMATION: Nucleotide aptamer sequence

<400> SEQUENCE: 138
uccaagcaua accugugucc gguagaucau gcccg                              35

<210> SEQ ID NO 139
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 139
ucacacggua cgugcaagca uccuacguuu gguca                              35

<210> SEQ ID NO 140
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 140
ucgccgggua cccauuccag gggggaucg gucgu                               35

<210> SEQ ID NO 141
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 141
ucgccgggua cccauuccag gggggaucg gucgg                               35

<210> SEQ ID NO 142
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 142
ucgccgggua cccauuccag gggggcucg gucgu                               35

<210> SEQ ID NO 143
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 143
acaggauggu uucgcuuuua gaugcgguaa gugca                              35

<210> SEQ ID NO 144
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 144
acaggauggu uucgcuuuua gaugcgggaa gugca                              35
```

<210> SEQ ID NO 145
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 145
acaggauggu uucgcuuuua gaugcgguaa gggca         35

<210> SEQ ID NO 146
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 146
acaggauggu uucgcuuuua gaugcgguaa gugcc         35

<210> SEQ ID NO 147
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 147
aaggcguuaa cgggaugcgu cucacgguca ucggc         35

<210> SEQ ID NO 148
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 148
acagggugac acccuccacu cguccucaau gugcc         35

<210> SEQ ID NO 149
<211> LENGTH: 35
<212> TYPE: RNA
<213> ORGANISM: Artificial sequence
<220> FEATURE:
<223> OTHER INFORMATION: Nucleotide aptamer sequence

<400> SEQUENCE: 149
gaauguacuu gguugcuccu ugccccgcg uaguc          35

<210> SEQ ID NO 150
<211> LENGTH: 38
<212> TYPE: DNA
<213> ORGANISM: Artificial sequence
<220> FEATURE:
<223> OTHER INFORMATION: Nucleotide aptamer sequence

<400> SEQUENCE: 150
ugguuccagu cggugaacuu ccugagu ccg gugugugc      38

<210> SEQ ID NO 151
<211> LENGTH: 38
<212> TYPE: DNA
<213> ORGANISM: Artificial sequence
<220> FEATURE:

```
<223> OTHER INFORMATION: Nucleotide aptamer sequence

<400> SEQUENCE: 151
uggagggcag cccgguaguc gcccacgggg aacgcguc                              38

<210> SEQ ID NO 152
<211> LENGTH: 36
<212> TYPE: DNA
<213> ORGANISM: Artificial sequence
<220> FEATURE:
<223> OTHER INFORMATION: Nucleotide aptamer sequence

<400> SEQUENCE: 152
uggcauacgc gcaggcugga gguauuaccc ccgggc                                36

<210> SEQ ID NO 153
<211> LENGTH: 22
<212> TYPE: DNA
<213> ORGANISM: Artificial sequence
<220> FEATURE:
<223> OTHER INFORMATION: 5' flanking sequence for aptamer candidates

<400> SEQUENCE: 153
acgacgctct tccgatctat gg                                               22

<210> SEQ ID NO 154
<211> LENGTH: 21
<212> TYPE: DNA
<213> ORGANISM: Artificial sequence
<220> FEATURE:
<223> OTHER INFORMATION: 3' flanking sequence to aptamer candidates

<400> SEQUENCE: 154
aagctaacgg agctcgtatg c                                                21

<210> SEQ ID NO 155
<211> LENGTH: 78
<212> TYPE: DNA
<213> ORGANISM: Artificial sequence
<220> FEATURE:
<223> OTHER INFORMATION: Nucleotide aptamer sequence with variable
      region flanked by two constant regions
<220> FEATURE:
<221> NAME/KEY: variation
<222> LOCATION: (23)..(57)
<223> OTHER INFORMATION: Any or all of nucleotide "n" at 23-57 can
      either be absent or present.
<220> FEATURE:
<221> NAME/KEY: misc_feature
<222> LOCATION: (23)..(57)
<223> OTHER INFORMATION: "n" is any nucleotide

<400> SEQUENCE: 155
acgacgctct tccgatctat ggnnnnnnnn nnnnnnnnnn nnnnnnnnnn nnnnnnnaag      60
ctaacggagc tcgtatgc                                                    78

<210> SEQ ID NO 156
<211> LENGTH: 37
<212> TYPE: DNA
<213> ORGANISM: Artificial sequence
<220> FEATURE:
<223> OTHER INFORMATION: PCR primer

<400> SEQUENCE: 156
taatacgact cactatagga cgacgctctt ccgatct                               37
```

```
<210> SEQ ID NO 157
<211> LENGTH: 21
<212> TYPE: DNA
<213> ORGANISM: Artificial sequence
<220> FEATURE:
<223> OTHER INFORMATION: PCR primer

<400> SEQUENCE: 157
gcatacgagc tccgttagct t                                              21

<210> SEQ ID NO 158
<211> LENGTH: 58
<212> TYPE: DNA
<213> ORGANISM: Artificial sequence
<220> FEATURE:
<223> OTHER INFORMATION: PCR primer

<400> SEQUENCE: 158
aatgatacgg cgaccaccga gatctacact ctttccctgg acgacgctct tccgatct     58

<210> SEQ ID NO 159
<211> LENGTH: 34
<212> TYPE: DNA
<213> ORGANISM: Artificial sequence
<220> FEATURE:
<223> OTHER INFORMATION: PCR primer

<400> SEQUENCE: 159
caagcagaag acggcatacg agctccgtta gctt                               34

<210> SEQ ID NO 160
<211> LENGTH: 33
<212> TYPE: DNA
<213> ORGANISM: Artificial sequence
<220> FEATURE:
<223> OTHER INFORMATION: Sequencing primer

<400> SEQUENCE: 160
acactctttc cctggacgac gctcttccga tct                                33
```